US012270031B2

(12) United States Patent
Zhu et al.

(10) Patent No.: US 12,270,031 B2
(45) Date of Patent: Apr. 8, 2025

(54) POLYPEPTIDE COMBINATION USED FOR TUMOUR IMMUNOTHERAPY, AND PREPARATION METHOD THEREFOR

(71) Applicants: Jecho Institute, Co., Ltd., Shanghai (CN); JECHO LABORATORIES, INC., Frederick, MD (US)

(72) Inventors: Jianwei Zhu, Shanghai (CN); Jing Wang, Shanghai (CN); Junsheng Chen, Shanghai (CN); Yueqing Xie, Shanghai (CN); Hua Jiang, Shanghai (CN); Huifang Zong, Shanghai (CN); Lei Han, Shanghai (CN)

(73) Assignees: Jecho Institute, Co., Ltd., Shanghai (CN); Jecho Laboratories, Inc., Frederick, MD (US)

( * ) Notice: Subject to any disclaimer, the term of this patent is extended or adjusted under 35 U.S.C. 154(b) by 757 days.

(21) Appl. No.: 17/605,472

(22) PCT Filed: Apr. 20, 2020

(86) PCT No.: PCT/CN2020/085736

§ 371 (c)(1),
(2) Date: Oct. 21, 2021

(87) PCT Pub. No.: WO2020/216194

PCT Pub. Date: Oct. 29, 2020

(65) Prior Publication Data

US 2022/0325286 A1 Oct. 13, 2022

(30) Foreign Application Priority Data

Apr. 22, 2019 (CN) ........................ 201910327356.9

(51) Int. Cl.

| | |
|---|---|
| ***C12N 15/62*** | (2006.01) |
| ***C07K 14/47*** | (2006.01) |
| ***C07K 19/00*** | (2006.01) |
| ***C12N 5/10*** | (2006.01) |
| ***C12P 21/02*** | (2006.01) |

(52) U.S. Cl.

CPC .............. *C12N 15/62* (2013.01); *C07K 14/47* (2013.01); *C07K 19/00* (2013.01); *C12N 5/10* (2013.01); *C12P 21/02* (2013.01)

(58) Field of Classification Search

None

See application file for complete search history.

(56) References Cited

U.S. PATENT DOCUMENTS

| | | | |
|---|---|---|---|
| 2018/0148508 | A1 | 5/2018 | Wang et al. |
| 2019/0062434 | A1 | 2/2019 | Han et al. |
| 2020/0115461 | A1 | 4/2020 | Evnin et al. |

FOREIGN PATENT DOCUMENTS

| | | | |
|---|---|---|---|
| CN | 105316353 A | | 2/2016 |
| CN | 105925596 A | | 9/2016 |
| CN | 106397599 A | | 2/2017 |
| CN | 107709356 A | | 2/2018 |
| CN | 109627340 A | | 4/2019 |
| WO | WO 2018/204717 | A1 | 11/2018 |
| WO | WO 2020/063880 | A1 | 4/2020 |

OTHER PUBLICATIONS

International Search Report issued on Jul. 21, 2020 in PCT/CN2020/085736 filed on Apr. 20, 2020, 5 pages.

Wang et al., "Reduction of non-specific toxicity of immunotoxin by intein mediated reconstitution on target cells", International Immunopharmacology, 2019, vol. 66, pp. 288-295.

Polu et al., "Probody therapeutics for targeting antibodies to diseased tissue", Expert Opinion on Biological Therapy, 2014, vol. 14, No. 8, pp. 1049-1053.

Riemer et al., "Generation of Peptide Mimics of the Epitope Recognized by Trastuzumab on the Oncogenic Protein Her-2/neu[1]", The Journal of Immunology, 2004, vol. 173, No. 1, pp. 394-401.

Extended European Search Report issued on Sep. 12, 2023 in the European Application No. 20796067.5, 13 pages.

Thomas Pirzer, et al., "Generation of Potent Anti-HER1/2 Immunotoxins by Protein Ligation Using Split Inteins", ACS Chemical Biology, vol. 13, No. 8, XP009511000, 2018, pp. 2058-2066.

*Primary Examiner* — Oluwatosin A Ogunbiyi

(74) *Attorney, Agent, or Firm* — Merchant & Gould P.C.; Daniel J. Pereira

(57) ABSTRACT

Provided is a polypeptide combination, a targeting component thereof comprising a shielding peptide, a cleavable part, an antigen-binding part and a first intein fragment, the shielding peptide and the antigen-binding part being connected by means of the cleavable part, and the antigen-binding part being directly or indirectly connected to the first intein fragment; a toxin component thereof comprises a second intein fragment and a toxin, and the second intein fragment is directly or indirectly connected to the toxin; the targeting component and the toxin component form an immunoconjugate by means of the interactive action between the first intein fragment and the second intein fragment; in the immunoconjugate, the shielding peptide and the antigen-binding part are connected by means of the cleavable part, and the antigen-binding part is connected to the toxin. Also provided are a preparation method and a pharmaceutical use for the polypeptide combination.

20 Claims, 5 Drawing Sheets

Specification includes a Sequence Listing.

POLYPEPTIDE COMBINATION USED FOR TUMOUR IMMUNOTHERAPY, AND PREPARATION METHOD THEREFOR

CROSS-REFERENCE TO RELATED APPLICATIONS

This application is a National Stage of PCT/CN2020/085736 filed Apr. 20, 2020 and claims the benefit of CN201910327356.9 filed Apr. 22, 2019.

TECHNICAL FIELD

The application relates to the field of biomedical, in particular to a polypeptide combination and a preparation method for tumor immunotherapy.

BACKGROUND

Recombinant immunotoxin is a therapeutic chimeric protein composed of cell targeting part and toxin part. It can specifically target and kill the diseased cells. It can be prepared by chemical coupling or gene recombination. When the recombinant immunotoxin works, it must bind to and be absorbed by the target cells, and the enzyme active fragment of the toxin must be transferred to the cytoplasm.

Shielding peptide can screen the antigen binding site of antibody or its antigen binding fragment, and reduce the non-specific binding of antibody or its antigen binding fragment in the process of circulation. When the antibody or its antigen binding fragment reaches the tumor microenvironment, the protease rich in the tumor micro-environment selectively cuts the linker peptide, removes the shielding peptide connected to the antibody or its antigen binding fragment through the linker peptide, restores the antigen binding ability of the antibody or its antigen binding fragment, so as to selectively kill the tumor cells and improve the killing specificity of the tumor.

Trans-splicing can be a protein splicing reaction mediated by a fragmented intein. For example, the N-terminus fragment and C-terminus segment of the protein containing peptide are identified and combined with non-covalent bonds, and the structure of the two fragments is folded correctly after the binding, and the protein extein on both sides of the protein intein is broken.

SUMMARY OF THE INVENTION

The present application provides a polypeptide combination for tumor immunotherapy and a preparation method thereof. The polypeptide combination and the preparation method have one or more of the following properties: 1) Improve drug safety and reduce non-specific toxicity to normal cells; 2) When located in a normal tissue, the immunoconjugate formed by the combination of the polypeptides cannot bind to the cells of the normal tissue and exert biological toxicity; When located in the tumor microenvironment, the immunoconjugate formed by the combination of polypeptides specifically binds to tumor-specific antigens on the surface of tumor cells, and exerts the ability to kill tumor cells and/or induce tumor cell apoptosis; 3) It has high flexibility and adjustability, for example, different administration methods, dosages and different administration combinations can be used to achieve better therapeutic effects 4) It can provide different targeting components for different tumor associated antigens; 5) The preparation method has universal applicability and can be applied to various types of immunotoxins or protein drugs; 6) It can be produced in eukaryotic expression system and prokaryotic expression system respectively to achieve industrialized high yield.

In one aspect, the present application provides a polypeptide combination, which comprises a targeting component and a toxin component, wherein the targeting component comprises a shielding peptide, cleavable part, an antigen-binding part and a first intein fragment, and the shielding peptide is connected with the antigen-binding part through the cleavable part, and the antigen-binding part is directly or indirectly connected with the first intein fragment; the toxin component comprises a second intein fragment and a toxin, and the second intein fragment is directly or indirectly connected with the toxin; the targeting component and the toxin component are able to form an immunoconjugate through the interaction between the first and second intein fragments; the immunoconjugate comprises the shielding peptide, the antigen-binding part and the toxin, wherein the shielding peptide is connected with the antigen-binding part through the cleavable partt, and the antigen-binding part is directly or indirectly connected with the toxin.

In some embodiments, the targeting component comprises a first polypeptide chain and a second polypeptide chain; the first polypeptide chain comprises the shielding peptide and the first antigen binding unit, and the shielding peptide is connected with the first antigen binding unit through the cleavable part; the second polypeptide chain comprises a second antigen binding unit and the first intein fragment, and the second antigen binding unit is directly or indirectly connected with the first intein fragment; and the first antigen binding unit and the second antigen binding unit are able to combine with each other to form the antigen-binding part.

In some embodiments, the second polypeptide chain and the toxin component can form a fusion peptide containing the second antigen binding unit and the toxin through the interaction between the first and second intein fragments; in the fusion polypeptide, the second antigen binding unit is directly or indirectly connected with the toxin; and the first polypeptide chain and the fusion polypeptide constitute the immunoconjugate.

In some embodiments, the immunoconjugate does not contain the first intein fragment and does not contain the second intein fragment.

In some embodiments, in the targeting component, the C-terminus of the shielding peptide is directly or indirectly connected with the N-terminus of the cleavable part.

In some embodiments, in the targeting component, the C-terminus of the cleavable part is directly or indirectly connected with the N-terminus of the antigen-binding part.

In some embodiments, in the targeting component, the C-terminus of the antigen-binding part is directly or indirectly connected with the N-terminus of the first intein fragment.

In some embodiments, in the first polypeptide chain, the C-terminus of the shielding peptide is directly or indirectly connected with the N-terminus of the cleavable part.

In some embodiments, in the first polypeptide chain, the C-terminus of the cleavable part is directly or indirectly connected with the N-terminus of the first antigen binding unit.

In some embodiments, in the second polypeptide chain, the C-terminus of the second antigen binding unit is directly or indirectly connected with the N-terminus of the first intein fragment.

In some embodiments, in the toxin portion, the C-terminus of the second intein is directly or indirectly connected with the N-terminus of the toxin.

In some embodiments, in the immunoconjugate, the C-terminus of the shielding peptide is directly or indirectly connected with the N-terminus of the cleavable part.

In some embodiments, in the immunoconjugate, the C-terminus of the cleavable part is directly or indirectly connected with the N-terminus of the antigen-binding part.

In some embodiments, in the immunoconjugate, the C-terminus of the antigen-binding part is directly or indirectly connected with the N-terminus of the toxin.

In some embodiments, in the immunoconjugate, the first polypeptide chain and the fusion polypeptide form the immunoconjugate through the mutual binding of the first antigen binding unit and the second antigen binding unit.

In some embodiments, in the fusion peptide, the C-terminus of the second antigen binding unit is directly or indirectly connected with the N-terminus of the toxin.

In some embodiments, the indirect connection includes a connection via a connector.

In some embodiments, the linker comprises a peptide linker comprising an amino acid sequence as shown in SEQ ID No: 11.

In some embodiments, the shielding peptides are selected from the following groups: a HER2 antigen shielding peptides, an EGFR antigen shielding peptides, an EpCAM antigen shielding peptides, and a Mesothelin antigen shielding peptides. In some embodiments, the shielding peptide comprises an amino acid sequence as shown in SEQ ID No: 1.

In some embodiments, the cleavable part selects the following groups: a matrix metalloproteinase sensitive linker, a serine protease sensitive linker, and an urokinase plasminogen activator sensitive linker. In some embodiments, the cleavable part contains the amino acid sequence shown in SEQ ID No: 2.

In some embodiments, the targeting component targets a tumor specific antigen. In some embodiments, the tumor specific antigen comprises HER2. In some embodiments, the antigen-binding part comprises an antibody or an antigen binding fragment thereof. In some embodiments, the first antigen binding unit and the second antigen binding unit are derived from the same antibody or antigen binding fragment thereof. In some embodiments, the antibodies are selected from the following groups: monoclonal antibodies, single chain antibodies, chimeric antibodies, humanized antibodies, and fully human antibodies. In some embodiments, the antigen binding fragment is selected from the following group: Fab, Fab', $F(ab')_2$, $F(ab)_2$, dAb, a separated complementary determining regions CDR, Fv and scFv. In some embodiments, the antigen binding fragment is a Fab.

In some embodiments, the first antigen binding unit comprises an amino acid sequence as shown in SEQ ID No: 3.

In some embodiments, the second antigen binding unit comprises an amino acid sequence as shown in SEQ ID No: 5.

In some embodiments, the toxins are selected from the following group: bacterial toxins, human toxins, and phytotoxins. In some embodiments, the toxins are selected from the following groups: *Pseudomonas aeruginosa* exotoxins and diphtheria toxins. In some embodiments, the toxins are selected from the following group: Ricin, Saporin and Gelonin. In some embodiments, the toxin comprises the amino acid sequence shown in SEQ ID No: 9.

In some embodiments, the first intein fragments and/or the second intein fragments contain a cleaved intein. In some embodiments, the fragmented inteins are selected from the following group: SsP DnaB, Ssp DnaE, and Npu DnaE.

In some embodiments, the first intein fragment is different from the second intein fragment.

In some embodiments, the first intein fragment and the second intein fragments are derived from the same intein.

In some embodiments, the first intein fragment comprises an amino acid sequence as shown in SEQ ID No: 6.

In some embodiments, the second intein fragment comprises an amino acid sequence as shown in SEQ ID No: 8.

In some embodiments, the first polypeptide chain comprises an amino acid sequence as shown in SEQ ID No: 4.

In some embodiments, the second polypeptide chain comprises an amino acid sequence as shown in SEQ ID No: 7.

In some embodiments, the toxin component comprises an amino acid sequence as shown in SEQ ID No: 10.

In some embodiments, the immunoconjugate comprises the amino acid sequences shown in SEQ ID No: 4 and SEQ ID No: 12.

In some embodiments, the fusion peptide comprises an amino acid sequence as shown in SEQ ID No: 12.

In another aspect, the present application provides a method for preparing an immunoconjugate, which includes the following steps: 1) providing a targeting component, the targeting component comprises a shielding peptide, a cleavable part, an antigen-binding part and a first intein fragment, and the shielding peptide is connected with the antigen-binding part through the cleavable part, and the antigen-binding part is directly or indirectly connected with the first intein fragment; 2) providing a toxin component comprising a second intein fragment and a toxin, and the second intein fragment is directly or indirectly connected with the toxin; 3) contacting the targeted component and the toxin component under the condition that the first intein fragments and the second intein fragments are able to interact, wherein the targeted component and the toxin component form the immunoconjugate through the interaction between the first intein fragments and the second intein fragments.

In some embodiments, the providing targeting component includes: providing a first polypeptide chain, the first polypeptide chain comprises the shielding peptide and a first antigen binding unit, and the shielding peptide is connected with the first antigen binding unit through the cleavable part; a second polypeptide chain is provided, the second polypeptide chain comprises a second antigen binding unit and the first intein fragment, and the second antigen binding unit is directly or indirectly connected with the first intein fragment; and combining the first polypeptide chain with the second polypeptide chain to form the targeted component, wherein the first antigen binding unit of the first polypeptide chain and the second antigen binding unit of the second polypeptide chain are combined with each other to form the antigen-binding part of the targeted component.

In some embodiments, wherein 3) includes making the second polypeptide chain and the toxin component form a fusion polypeptide containing the second antigen binding unit and the toxin through the interaction between the first intein fragment and the second intein fragment, and the fusion polypeptide and the first polypeptide chain form the immunoconjugate.

In some embodiments, the immunoconjugate does not include the first intein fragment and does not include the second intein fragment.

In some embodiments, in the targeting component, the C-terminus of the shielding peptide is directly or indirectly connected to the N-terminus of the cleavable part.

In some embodiments, in the targeting component, the C-terminus of the cleavable part is directly or indirectly connected to the N-terminus of the antigen-binding part.

In some embodiments, in the targeting component, the C-terminus of the antigen-binding part is directly or indirectly connected to the N-terminus of the first intein fragment.

In some embodiments, in the first polypeptide chain, the C-terminuss of the shielding peptide is directly or indirectly connected to the N-terminus of the cleavable part.

In some embodiments, in the first polypeptide chain, the C-terminus of the cleavable part is directly or indirectly connected to the N-terminus of the first antigen binding unit.

In some embodiments, in the second polypeptide chain, the C-terminus of the second antigen binding unit is directly or indirectly connected to the N-terminus of the first intein fragment.

In some embodiments, in the toxin portion, the C-terminus of the second intein is directly or indirectly connected to the N-terminus of the toxin.

In some embodiments, in the immunoconjugate, the C-terminus of the shielding peptide is directly or indirectly connected to the N-terminus of the cleavable part.

In some embodiments, in the immunoconjugate, the C-terminus of the cleavable part is directly or indirectly connected to the N-terminus of the antigen-binding part.

In some embodiments, in the immunoconjugate, the C-terminus of the antigen-binding part is connected directly or indirectly to the N-terminus of the toxin.

In some embodiments, in the immunoconjugate, the first polypeptide chain and the fusion polypeptide via the first antigen-binding unit and the second antigen-binding unit mutually combined constitute the immunoconjugates.

In some embodiments, in the fusion polypeptide, the C-terminus of the second antigen-binding unit is connected directly or indirectly to the N-terminus of the toxin.

In some embodiments, the indirect connection consists of a connection through a linker. In some embodiments, the linker comprises a peptide linker, the peptide linker comprises the amino acid sequence shown in SEQ ID NO: 11.

In some embodiments, the shielding peptide is selected from the following group: a HER2 antigen shielding peptide, a EGFR antigen shielding peptide, a EpCAM antigen shielding peptide and a Mesothelin antigen shielding peptide.

In some embodiments, the shielding peptide comprises the amino acid sequence shown in SEQ ID NO:1.

In some embodiments, the cleavable part is selected from the following group: a matrix metalloproteinase-sensitive linker, a serine protease-sensitive linker, and an urokinase plasminogen activator-sensitive linker.

In some embodiments, the cleavable part contains an amino acid sequence as shown in SEQ ID NO:2.

In some embodiments, the targeting component targets tumor-specific antigens. In some embodiments, the tumor-specific antigen comprises HER2. In some embodiments, the antigen-binding part comprises an antibody or antigen-binding fragment. In some embodiments, the first antigen-binding unit and the second antigen-binding unit are derived from the same antibody or antigen-binding fragment. In some embodiments, the antibodies are selected from the following Description group: monoclonal antibodies, single chain antibodies, chimeric antibodies, humanized antibodies, and fully human antibodies. In some embodiments, the antigen binding fragments are selected from the following groups: Fab, Fab', $F(ab')_2$, $F(ab)_2$, dAb, the separate complementarity-determining regions CDR, Fv, and scFv. In some embodiments, the antigen-binding fragment is Fab. In some embodiments, the first antigen binding unit comprises the amino acid sequence shown in SEQ ID NO:3.

In some embodiments, the second antigen binding unit comprises the amino acid sequence shown in SEQ ID NO:5.

In some embodiments, the toxins are selected from the following groups: a bacterial toxins, a human toxins, and a plant toxins. In some embodiments, the toxins are selected from the following groups: *Pseudomonas aeruginosa* exotoxins and diphtheria toxins. In some embodiments, the toxins are selected from the following groups: ricin, saporin and gelonin. In some embodiments, the toxin comprises the amino acid sequence shown in SEQ ID NO:9. In some embodiments, the first intein fragment and/or the second intein fragment comprises a fragmented intein. In some embodiments, the fragmented intein is selected from the following group: SsP DnaB, SsP DnaE, and Npu DnaE.

In some embodiments, the first intein fragment is different from the second intein fragment. In some embodiments, the first intein fragment and the second intein fragment are derived from the same intein. In some embodiments, the first intein fragment comprises the amino acid sequence as shown in SEQ ID NO:6.

In some embodiments, the second intein fragment comprises the amino acid sequence as shown in SEQ ID NO:8.

In some embodiments, the first polypeptide chain comprises the amino acid sequence as shown in SEQ ID NO:4.

In some embodiments, the second polypeptide chain comprises the amino acid sequence as shown in SEQ ID NO:7.

In some embodiments, the toxin component comprises the amino acid sequence as shown in SEQ ID NO:10.

In some embodiments, the immunoconjugate comprises the amino acid sequence as shown in SEQ ID NO:4 and SEQ ID NO:12.

In some embodiments, the fusion polypeptide comprises the amino acid sequence as shown in SEQ ID NO:12.

In some embodiments, the interaction between the first intein fragment and the second intein fragment comprises trans-splicing reaction.

In some embodiments, a reducing agent is used to initiate an interaction between the first intein fragment and the second intein fragment.

In some embodiments, the reducing agent is selected from the following group: DTT and β-mercaptoethanol. In some embodiments, the concentration of the reducing agent is 0.1-100 nM. In some embodiments, the reducing agent is in contact with the targeting component and the toxin component. In some embodiments, the method for preparing immunoconjugates also includes incubating after addition of the reducing agent. In some embodiments, the temperature of incubating is 1-50° C. In some embodiments, wherein the time of incubating ranges from 60 to 300 minutes. The present application provides a vector, comprising a nucleic acid encoding the first polypeptide chain in the polypeptide combination, a nucleic acid encoding the second polypeptide chain in the polypeptide combination, a nucleic acid encoding the toxin component in the polypeptide combination, a nucleic acid encoding the cleavable part of the polypeptide combination, a nucleic acid encoding the first antigen binding unit in the polypeptide combination, a nucleic acid encoding the second antigen binding unit in the polypeptide combination, and a nucleic acid encoding the toxin described in the polypeptide combination and/or the nucleic acid encoding the shielding peptide described in the polypeptide combination.

The present application provides a cell that expresses the vector.

The present application provides a use of the polypeptide combination, the vector or the cell in the preparation of a medicine for the treatment of a disease, and the disease include a tumor.

In some embodiments, the tumor includes ovarian cancer and breast cancer.

The present application provides the polypeptide combination, the vector or the cell, which treats tumors.

The present application provides a method for treating tumors, which comprises the application of the polypeptide combination, the vector or the cell.

Technical personnel in this field can easily perceive other aspects and advantages of the present application from the detailed description below. Only an example implementation of the present application is shown and described in the detailed description below. As technicians in the field will recognize, the contents of the present application enable technicians in the field to make changes to the specific implementations disclosed without separating them from the spirit and scope of the invention covered by the present application. Correspondingly, the description in the drawings and specifications attached to the present application is intended to be exemplary and not restrictive.

BRIEF DESCRIPTION OF THE DRAWINGS

The specific features of the invention involved in the present application are shown in the appended claims. The characteristics and advantages of the invention involved in the present application can be better understood by referring to the exemplary embodiments and the accompanying drawings described in detail below. A brief description of the attached drawings is as follows:

DETAILED DESCRIPTION OF THE EMBODIMENTS

Figure 1:
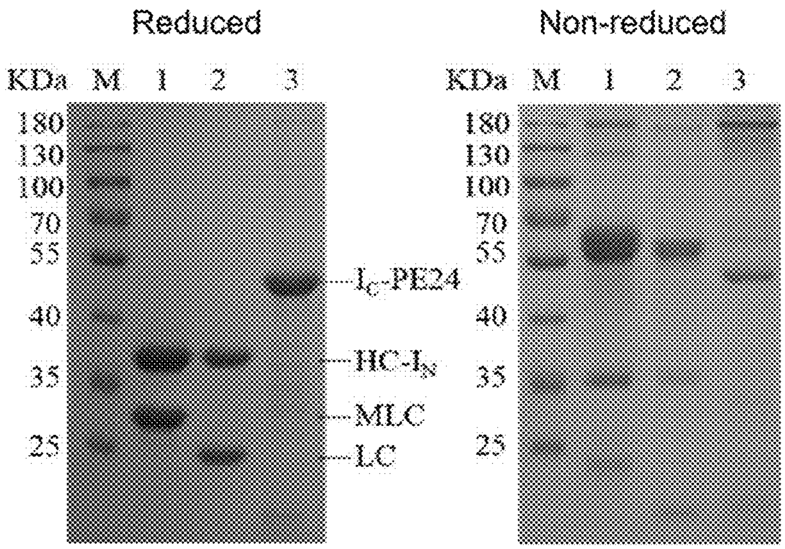
FIG. 1 shows the results of SDS-PAGE detection of the targeted components and toxin components in the present application.

The following specific examples illustrate the implementation of the invention of the present application. Those familiar with this technology can easily understand other advantages and effects of the invention of the present application from the content disclosed in this specification.

In the present application, the term “polypeptide combination” generally refers to a collection of two or more proteins or polypeptides. In the present application, the polypeptide combination may be a composition comprising two or more proteins or polypeptides. In the polypeptide combination of the present application, different proteins or polypeptides may be located in different containers or physical spaces, respectively. For another example, two or more different proteins or polypeptides may also be located in the same container or in the same physical space. In the present application, the polypeptide combination may not be a protein molecule or a protein complex. For example, none of the two or more proteins or polypeptides are located in the same protein molecule or in the same protein complex.

In the present application, the term “targeting component” generally refers to a protein or polypeptide comprising a shielding peptide, a cleavable part, an antigen-binding part and a first intein fragment. The targeting component may target tumor cells. For example, the antigen-binding part may specifically bind to tumor cells. In the targeting portion, the shielding peptide and the antigen-binding part may be connected through the cleavable part, and the antigen-binding part may be directly or indirectly connected to the first intein fragment.

In the present application, the term “shielding peptide” generally refers to a polypeptide or a fragment that binds to the antigen-binding part and prevents the antigen-binding part from binding to the antigen. For example, the shielding peptide may be located at the N-terminus of the antigen-binding part. For example, the shielding peptide may be connected to the antigen-binding part through a cleavable part. In the present application, when the shielding peptide is located in the environment of normal tissues, the shielding peptide cannot be separated from the antigen-binding part to which it is attached, making the antigen-binding part unable to bind to the antigen. When the shielding peptide is located in the tumor environment, the tumor cell releases specific proteases that allow the shielding peptide to be separated from the antibody-binding portion to which it is attached (for example, by cutting off the cleavable part) so that the antigen-binding part may bind to the antigen of the tumor cells. In the present application, the shielding peptide may be the shielding peptide used in Probody technology (see, Polu K R, Lowman H B. Probody therapeutics for targeting antibodies to diseased tissue. Expert Opinion on Biological Therapy. 2014;14:1049-1053).

In the present application, the term “cleavable part” generally refers to a polypeptide or fragment thereof with cleavable properties that connects the shielding peptide and the antigen-binding part. In the present application, the cleavable part may be cleaved by the action of a protease. For example, the cleavable part may be cleaved by proteases in the tumor environment (for example, proteases enriched around tumor cells), thereby separating the shielding peptide from the antigen-binding part. For example, the isolated antigen-binding part may be bound to a tumor-specific antigen.

In the present application, the term “antigen-binding part” generally refers to an antibody or antigen-binding fragment thereof that can bind to a tumor-specific antigen.

In the present application, the term “tumor-specific antigen” generally refers to an antigen that is specifically expressed on the surface of one or more tumor cells and is almost absent on normal cells.

In the present application, the term "HER2" generally refers to human epidermal growth factor receptor 2, and may also be referred to as Neu, ErbB-2 or CD340. The HER2 may be a protein encoded by the ERBB2 gene, which belongs to a member of the epidermal growth factor receptor (EGFR/ErbB) family. The recombinant humanized trastuzumab (Herceptin®) can specifically bind to the extra-cellular fourth subdomain of HER2. The HER2 may belong to the tumor-specific antigen, for example, it may be a target for breast cancer or ovarian cancer. The accession number of human HER2 in GenBank may be NP_001276866.1.

In the present application, the term "antibody" generally refers to a polypeptide molecule capable of specifically recognizing and/or neutralizing a specific antigen. The basic four-chain antibody unit is a heterotetrameric glycoprotein, which is composed of two identical light chains and two identical heavy chains. In the case of IgG, each L chain is connected to the H chain by a covalent disulfide bond, and two H chains are connected to each other by one or more disulfide bonds. The number of disulfide bonds depends on the homotype of the H chain. Each H and L chain also has regularly spaced intrachain disulfide bonds. Each H chain has a variable domain (VH) at the N-terminus, followed by three (for each $\alpha$ and $\gamma$ chain) or four (for $\mu$ and $\epsilon$ isotypes) constant domain (CH).

In the present application, the term "antigen-binding fragment" generally refers to a part of a complete antibody, for example, the antigen-binding fragment may be the antigen-binding region and/or antibody variable region of a complete antibody. The antigen-binding fragment may be obtained by chemical methods and/or genetic engineering methods. For example, proteases, including pepsin and papain, may be used to digest antibodies to produce antigen-binding fragments.

In the present application, the term "Fab" generally refers to the production of two identical antigen-binding fragments after papain digests an antibody with a complete structure (for example, the Fc region and the hinge region are removed). The Fab may be composed of a complete light chain, the variable region of the heavy chain (VH), and the first constant domain (CH1) of the heavy chain. Each Fab may have a single antigen binding site.

In the present application, the term "Fab" generally refers to an antigen-binding fragment with several additional residues at the carboxyl terminal of the CH1 domain compared to the Fab, and Fab' includes one or more cysteines from the antibody hinge region.

In the present application, the term "$F(ab)_2$" generally refers to an antigen-binding fragment obtained from a pair of Fab linked by cysteine.

In the present application, the term "Fv" generally refers to an antigen-binding fragment composed of the VL and VH domains of a single arm of an antibody.

In the present application, the term "single-chain antibody (scFv)" generally refers to a molecule consisting of the heavy and light chain variable regions of the antibody linked by a short peptide linker.

In the present application, the term "intein" generally refers to an inserted sequence located in the host protein. The intein needs to be inserted into the extein gene to be able to replicate and transcribe, and may be excised from the precursor protein and connect the extein on both sides to form a mature protein. For example, the nucleotide sequence corresponding to the intein may be chimeric in the nucleic acid sequence corresponding to the host protein, exist in the same open reading frame as the host protein gene, and be transcribed and translated synchronously with the host protein gene. After the protein precursor, the intein is excised from the host protein to form a mature active protein. According to the existence form of intein, it may be divided into whole intein and fragmented intein. For example, the two splicing regions of the whole intein may coexist in the same polypeptide fragment; and the two splicing regions of the fragmented intein may be split into two or more fragments and exist in different polypeptide fragments.

In the present application, the term "fragmented intein" generally refers to an intein in which two cleavage regions may be located in more than two polypeptide fragments. For example, the fragmented intein may include an N-terminus protein splicing region (N fragment of intein, In) and a C-terminus protein splicing region (C fragment of intein, Ic). Wherein, the N-terminus of the N-terminus protein splicing region may be connected to an extein (for example, N-extein); the C-terminus of the C-terminus protein splicing region may be connected to another extein (for example, C-extein). For example, the N-extein and the C-extein may be located in two different open reading frames. For example, under a suitable environment, through the interaction between the N-terminus protein splicing region and the C-terminus protein splicing region belonging to the same fragmented intein, the N-terminus protein splicing region and the C-terminus protein splicing region may be excised, and the N-extein and the C-extein may be connected to each other to form a connected protein or polypeptide.

In the present application, the term "first intein fragment" usually refers to a partial fragment of intein, which may not include a complete intein fragment. Under certain conditions, the first intein fragment may interact with other intein fragments in such a way that the protein or polypeptide fragment attached to the first intein fragment (such as an extein) is connected to another protein or polypeptide fragment (such as an extein) to form a linked protein or polypeptide. For example, the first intein fragment may be linked to a second antigen binding unit.

In the present application, the term "second intein fragment" generally refers to a partial fragment of the intein, which may not include a complete intein fragment. In the present application, the second intein fragment may be different from the first intein fragment. For example, the first intein fragment may be derived from the same intein as the second intein fragment. In the present application, under certain conditions, the second intein fragment may interact with the first intein fragment. For example, the second intein fragment may interact with other intein fragments, so that the protein or polypeptide fragment (such as extein, for example, toxin) connected to the second intein fragment may interact with other protein or polypeptide fragments (such as extein) to form a connected protein or polypeptide. In the present application, the second intein fragment may be linked to a toxin. For example, the first intein fragment may interact with the second intein fragment so that the second antigen binding unit and the toxin form a fusion polypeptide.

In the present application, the term "toxin" generally refers to a poison produced by an organism. The toxins are usually proteins that interfere with the action of other macromolecules in the organism, and the toxins may usually function by inhibiting protein synthesis through enzymatic hydrolysis. Toxins may include bacterial toxins, phytotoxins and human toxins according to their sources. For example, the bacterial toxins may include *Pseudomonas aeruginosa* exotoxin (PE) and diphtheria toxin (DT). The phytotoxin may include ricin, saponin and gelonin. Generally, toxins may include the following functional areas: cell binding area, translocation area, and toxic activity area. For example, the cell binding zone may enrich the toxin on the surface of the target cell.

In the present application, the term "PE24" generally refers to the fragment of *Pseudomonas aeruginosa* exotoxin (PE) after the cell binding region is truncated. The complete PE contains three functional areas, namely the cell binding area (Ia area, 1-252aa), the translocation area (II area, 253-364aa) and the toxic activity area (III area, 400-613aa). The PE truncated body PE24 truncated the cell binding region (Ia region, 1-252aa), and further truncated to remove the TB cell epitope, greatly reducing the immunogenicity of the toxin (see, Mazor R, Onda M, Park D, et al. Dual B- and T-cell de-immunization of recombinant immunotoxin targeting mesothelin with high cytotoxic activity. Oncotarget. 2016;7:29916-29926.). The amino acid sequence of PE24 may be as shown in SEQ ID NO.9.

In the present application, the term "toxin component" generally refers to a protein or polypeptide comprising the second intein fragment and the toxin. In the present application, the toxin component may have biological toxicity, and the biological toxicity may be produced by the toxin. In the present application, the second intein fragment in the toxin component may interact with the first intein fragment in the targeting component to produce the immunoconjugate of the shielding peptide, the cleavable part, the antigen-binding part and the toxin.

In the present application, the term "interaction" generally refers to the interaction between the first intein fragment and the second intein fragment. In the present application, after the interaction, the protein or polypeptide multi-linked by the first intein fragment may be linked to the protein or polypeptide connected by the second intein fragment to form a connected protein or polypeptide. For example, the interaction may be splicing. For example, the interaction may be protein trans-splicing. For example, the first intein fragment and the second intein fragment may undergo protein trans-splicing to make the second antigen binding unit and the toxin form the fusion polypeptide.

In the present application, the term "protein trans-splicing" refers to a protein splicing reaction mediated by a fragmented protein intein. For example, the N-terminus fragment (In) of the fragmented intein and the C-terminus fragment (Ic) of the fragmented intein recognize each other and are bonded by a non-covalent bond. The combination folds the structure correctly and is removed by trans-cleavage, and the N-terminus fragment of the fragmented intein is connected to the extein on both sides of the C-terminus fragment of the fragmented intein, so as to obtain the protein formed by the exteins on both sides.

In the present application, the term "first polypeptide chain" generally refers to a single polypeptide chain comprising the shielding peptide and the first antigen binding unit. In the first polypeptide chain, the shielding peptide and the first antigen binding unit may be connected through the cleavable part.

In the present application, the term "first antigen binding unit" generally refers to a part of the antigen-binding part. The first antigen binding unit has the ability to specifically bind to the tumor-specific antigen. In the present application, the first antigen-binding unit may be an antibody part or an antigen-binding fragment thereof that specifically binds to the tumor-specific antigen. For example, the first antigen binding unit may be a light chain (LC) of an antibody that specifically binds to the tumor-specific antigen.

In the present application, the term "second polypeptide chain" generally refers to a single polypeptide chain comprising a second antigen binding unit and the first intein fragment. In the second polypeptide chain, the second antigen binding unit and the first intein fragment may be directly or indirectly connected.

In the present application, the term "second antigen binding unit" generally refers to a part of the antigen-binding part. The second antigen binding unit has the ability to specifically bind to the tumor-specific antigen. In the present application, the second antigen-binding unit may be an antibody portion or an antigen-binding fragment thereof that specifically binds to the tumor-specific antigen. In the present application, the second antigen binding unit may be different from the first antigen binding unit. In the present application, the second antigen-binding unit may be combined with the first antigen-binding unit to form the antigen-binding part. For example, the second antigen binding unit may be the CH1 portion of the variable region and the constant region of the heavy chain of an antibody that specifically binds to the tumor-specific antigen. For another example, the second antigen binding unit may be the variable region of the heavy chain of the antibody that specifically binds to the tumor-specific antigen, the CH1 portion of the constant region, and the hinge region. In the present application, the second antigen-binding unit may bind to the first antigen-binding unit to form a Fab that specifically binds to the tumor-specific antigen.

In the present application, the term "fusion polypeptide" generally refers to a protein or polypeptide comprising the second antigen binding unit and the toxin. In the present application, the fusion polypeptide may be formed by the interaction of the first intein fragment in the second polypeptide chain and the second intein fragment in the toxin component. For example, the interaction may be protein trans-splicing of the first intein fragment and the second intein fragment.

In the present application, the term "immunoconjugate" generally refers to a protein or polypeptide containing the shielding peptide, the antigen-binding part, and the toxin. In the present application, in the immunoconjugate, the shielding peptide and the antigen-binding part are connected through the cleavable part, and the antigen-binding part is directly or indirectly connected to the toxin. For example, the indirect connection may be a connection through a linker. In the present application, the immunoconjugate may include the shielding peptide, the antigen-binding part, and the toxin in sequence from N-terminus to C-terminus. For example, the immunoconjugate may sequentially include the shielding peptide, the cleavable part, the antigen-binding part, and the toxin from N-terminus to C-terminus. In the present application, the immunoconjugate may have both biological toxicity and the property of specifically targeting tumors.

In the present application, the term "linker" generally refers to a molecule used to link two or more proteins or polypeptides. In the present application, the indirect connection between different proteins or polypeptides may be achieved through the linker. In the present application, the linker may be a peptide linker. For example, the second antigen binding unit may be connected to the toxin through the linker.

In the present application, the term "N-terminus" generally refers to the end of a polypeptide chain, which may have an a-amino amino acid residue.

In the present application, the term "C-terminus" generally refers to the end of a polypeptide chain, which may have an α-carboxyl amino acid residue. For a polypeptide chain, the N-terminus is the end of one end, and the C-terminus may be the end on the other side that is different from the N-terminus.

In the present application, the term "reducing agent" generally refers to an agent capable of initiating the interaction between the first intein fragment and the second intein fragment. In the present application, the reducing agent may initiate protein trans-splicing between the first intein fragment and the second intein fragment. For example, the reducing agent may be a reagent that loses electrons in a redox reaction. For example, the reducing agent may be DTT (Dithiothreitol, molecular formula is C4H10O2S2).

In the present application, the term "comprising" generally refers to the inclusion of explicitly specified features, but not excluding other elements.

In the present application, the term "about" generally refers to a range of 0.5%-10% above or below the specified value, such as 0.5%, 1%, 1.5%, 2%, 2.5%, above or below the specified value. Changes within the range of 3%, 3.5%, 4%, 4.5%, 5%, 5.5%, 6%, 6.5%, 7%, 7.5%, 8%, 8.5%, 9%, 9.5%, or 10%.

Polypeptide Combination and Preparation Method

The present application provides a polypeptide combination, which includes a targeting component and a toxin component, including: the targeting component contains a shielding peptide, a cleavable part, an antigen-binding part and a first intein fragment, the shielding peptide and the antigen-binding part are connected through the cleavable part, and the antigen-binding part is directly or indirectly connected to the first intein fragment; the toxin component includes a second intein fragment and a toxin, and the second intein fragment is directly or indirectly connected to the toxin; the targeting component and the toxin component may form an immunoconjugate by the interaction between the first and second intein fragments. The immunoconjugate comprises the shielding peptide, the antigen-binding part, and the toxin, wherein the shielding peptide and the antigen-binding part are connected by the cleavable part, and the antigen-binding part is connected directly or indirectly to the toxin.

The present application also provides a method for preparing an immunoconjugate, which includes the following steps: 1) Providing a targeting component, the targeting component comprising a shielding peptide, a cleavable part, an antigen-binding part and a first intein fragment, the shielding peptide and the antigen-binding part are connected through the cleavable part, and the antigen-binding part is directly or indirectly connected to the first intein fragment; 2) Providing a toxin component, the toxin component comprising a second intein fragment and a toxin, and the second intein fragment is directly or indirectly connected to the toxin; 3) Contacting the targeting component and the toxin component under conditions that enable the first intein fragment and the second intein fragment to interact, wherein the targeting component and the toxin component form the immunoconjugate by interaction between the first and second intein fragments.

Targeting Component

In the present application, the targeting component may include a shielding peptide, a cleavable part, an antigen-binding part, and a first intein fragment, wherein the shielding peptide may interact with the antigen-binding part through the cleavable part, and the antigen-binding part may be directly or indirectly connected to the first intein fragment.

In the targeting component of the present application, the C-terminus of the shielding peptide may be directly or indirectly connected to the N-terminus of the cleavable part.

In the present application, the shielding peptide may be selected from the following group: HER2 antigen shielding peptide, EGFR antigen shielding peptide, EpCAM antigen shielding peptide and Mesothelin antigen shielding peptide. In the present application, the shielding peptide may comprise the amino acid sequence shown in SEQ ID NO:1.

In the targeting component of the present application, the C-terminus of the cleavable part may be directly or indirectly connected to the N-terminus of the antigen-binding part.

In the present application, the cleavable part may be selected from the following groups: matrix metalloproteinase-sensitive linker, serine protease-sensitive linker, and urokinase plasminogen activator-sensitive linker. In the present application, the cleavable part may comprise the amino acid sequence shown in SEQ ID NO:2.

In the targeting component of the present application, the C-terminus of the antigen-binding part may be directly or indirectly connected to the N-terminus of the first intein fragment.

In the present application, the first intein fragment may comprise the amino acid sequence shown in SEQ ID NO:6.

In the present application, the targeting component may target tumor-specific antigens. For example, the tumor-specific antigen may comprise HER2.

In the present application, the antigen-binding part may comprise an antibody or an antigen-binding fragment. For example, the antibody may be selected from the group consisting of monoclonal antibodies, single chain antibodies, chimeric antibodies, humanized antibodies, and fully human antibodies. For another example, the antigen-binding fragment may be selected from the group consisting of Fab, Fab', F(ab')2, F(ab)2, dAb, isolated complementarity determining region CDR, Fv and scFv. In the present application, the antigen-binding fragment may be Fab.

The First Polypeptide Chain In the present application, the targeting component may include a first polypeptide chain and a second polypeptide chain, wherein the first polypeptide chain may include the shielding peptide and the first antigen binding unit, the shielding peptide may be connected to the first antigen binding unit through the cleavable part.

In the first polypeptide chain of the present application, the C-terminus of the shielding peptide may be directly or indirectly connected to the N-terminus of the cleavable part.

In the first polypeptide chain of the present application, the C-terminus of the cleavable part may be directly or indirectly connected to the N-terminus of the first antigen binding unit.

In the present application, the first antigen binding unit may comprise the amino acid sequence shown in SEQ ID NO:3.

In the first polypeptide chain of the present application, from the N-terminus to the C-terminus, it may include the shielding peptide, the cleavable part, and the first antigen binding unit in sequence. For example, the first polypeptide chain may include the shielding peptide (which may include the amino acid sequence shown in SEQ ID NO: 1) and the cleavable part (which may include the amino acid sequence shown in SEQ ID NO: 2) and the first antigen binding unit (which may be the light chain of trastuzumab, which may include the amino acid sequence shown in SEQ ID NO: 3) from the N-terminus to C-terminus.

For example, the first polypeptide chain may be PM-MLC, which may include the amino acid sequence shown in SEQ ID NO:4. In the present application, the first polypeptide chain may comprise the amino acid sequence shown in SEQ ID NO:4.

The second polypeptide chain In the present application, the second polypeptide chain may include a second antigen-binding unit and the first intein fragment, and the second antigen-binding unit may be directly or indirectly connected to the first intein fragment.

In the second polypeptide chain of the present application, the C-terminus of the second antigen binding unit may be directly or indirectly connected to the N-terminus of the first intein fragment.

In the present application, the second antigen binding unit may comprise the amino acid sequence shown in SEQ ID NO:5.

In the second polypeptide chain of the present application, it may sequentially include the second antigen binding unit and the first intein fragment from the N-terminus to the C-terminus. For example, the second polypeptide chain may include the second antigen binding unit (which may be the variable region and CH1 of the heavy chain of trastuzumab, which may include the amino acid sequence in SEQ ID NO: 5) and the first intein fragment (which may include the amino acid sequence shown in SEQ ID NO: 6) from the N-terminus to C-terminus.

For example, the second polypeptide chain may be PM-HC-In, which may include the amino acid sequence shown in SEQ ID NO:7. In the present application, the second polypeptide chain may comprise the amino acid sequence shown in SEQ ID NO:7.

In the present application, the first antigen-binding unit in the first polypeptide chain may bind to the second antigen-binding unit in the second polypeptide chain to form the antigen-binding part. For example, the first antigen-binding unit and the second antigen-binding unit may be derived from the same antibody or antigen-binding fragment.

For example, the first antigen binding unit and the second antigen binding unit may be derived from trastuzumab. For example, the first antigen binding unit may be the light chain of trastuzumab, and the second antigen binding unit may be the variable region and constant region CH1 region of the heavy chain of trastuzumab. For example, the first antigen binding unit may include the amino acid sequence shown in SEQ ID NO: 3, and the second antigen binding unit may include the amino acid sequence shown in SEQ ID NO: 5.

In the present application, the first antigen binding unit and the second antigen binding unit may form a Fab.

In the present application, the first polypeptide chain and the second polypeptide chain may be expressed in an expression system of eukaryotic cells.

Toxin Component

In the present application, the toxin component may comprise a second intein fragment and a toxin, wherein the second intein fragment may be directly or indirectly linked to the toxin.

In the present application, the second intein fragment may comprise the amino acid sequence shown in SEQ ID NO:8.

In the present application, the toxin may be selected from the following group: bacterial toxins, human toxins and phytotoxins. For example, the toxin may be selected from the group of *Pseudomonas aeruginosa* exotoxin and diphtheria toxin. For example, the toxin may be selected from the group consisting of ricin, saponin and gelonin. In the present application, the toxin may comprise PE24. For example, the toxin may comprise the amino acid sequence shown in SEQ ID NO:9.

In the toxin component of the present application, the C-terminus of the second intein is directly or indirectly connected to the N-terminus of the toxin.

In the present application, the indirect connection may include connection through a linker. For example, the linker may comprise a peptide linker. For example, the peptide linker may include the amino acid sequence shown in SEQ ID NO:1.

In the toxin component of the present application, it may sequentially include the second intein fragment and the toxin from N-terminus to C-terminus. For example, in the toxin component, it may sequentially include the second intein fragment, the linker, and the toxin from N-terminus to C-terminus. For example, in the toxin component, it may sequentially include the second intein fragment (which may include the amino acid sequence shown in SEQ ID NO: 8), the linker (which may include the amino acid sequence shown in SEQ ID NO: 11) and the toxin PE24 (which may include the amino acid sequence shown in SEQ ID NO: 9) from N-terminus to C-terminus.

For example, the toxin component may be Ic-PE24, which may include the amino acid sequence shown in SEQ ID NO:10. In the present application, the toxin component may comprise the amino acid sequence shown in SEQ ID NO:10.

In the present application, the toxin component may be expressed in the expression system of prokaryotic cells.

In the present application, the targeting component and the toxin component may form an immunoconjugate through the interaction between the first intein fragment and the second intein fragment.

In the present application, the first intein fragment may be different from the second intein fragment.

In the present application, the first intein fragment and the second intein fragment may be derived from the same intein. In the present application, the first intein fragment and/or the second intein fragment may comprise a fragmented intein. In the present application, the fragmented intein may be selected from the following group: SsP DnaB, Ssp DnaE and Npu DnaE.

In the present application, the first intein fragment may be the N-terminus fragment of Npu DnaE, and the second intein fragment may be the C-terminus part of Npu DnaE. For example, the first intein fragment and the second intein fragment may form a complete fragmented intein Npu DnaE. For example, the first intein fragment may include the amino acid sequence shown in SEQ ID NO: 6, and the second intein fragment may include the amino acid sequence shown in SEQ ID NO: 8.

Fusion Polypeptide

In the present application, the second polypeptide chain and the toxin component may form a fusion polypeptide containing the second antigen-binding unit and the toxin through the interaction between the first intein fragment and the second intein fragment.

In the present application, the interaction may be trans-splicing. For example, it may be a fragmented intein (for example, Npu DnaE)-mediated trans-splicing of a protein. In the present application, due to the interaction between the first intein fragment and the second intein fragment, the first intein fragment and the second intein fragment are removed after being connected, so that the second antigen-binding unit linked to the first intein fragment and the toxin linked to the second intein fragment are connected to each other to form the second antigen-binding unit and the Fusion polypeptide of toxin.

In the fusion polypeptide of the present application, the second antigen binding unit may be directly or indirectly connected to the toxin. In the fusion polypeptide of the present application, the C-terminus of the second antigen binding unit may be directly or indirectly connected to the N-terminus of the toxin.

In the present application, the indirect connection may include connection through a linker. For example, the linker may comprise a peptide linker. For example, the peptide linker may include the amino acid sequence shown in SEQ ID NO:11.

In the fusion polypeptide described in the present application, it may sequentially include the second antigen binding unit and the toxin from N-terminus to C-terminus. For example, it may include the second antigen binding unit, the linker and the toxin in sequence from the N-terminus to the C-terminus. For example, the fusion polypeptide may sequentially include the second antigen binding unit (which may be the variable region and CH1 of the heavy chain of trastuzumab, which may include the amino acid sequence in SEQ ID NO: 5), the linker (which may include the amino acid sequence shown in SEQ ID NO: 11), and the toxin PE24 (which may include the amino acid sequence of SEQ ID NO: 9 from the N-terminus to C-terminus.

In the present application, the fusion polypeptide may comprise the amino acid sequence shown in SEQ ID NO:12.

Immunoconjugate

In the present application, the immunoconjugate may include the shielding peptide, the antigen-binding part, and the toxin, wherein the shielding peptide and the antigen-binding part may be connected through the cleavable part, and the antigen-binding part may be directly or indirectly linked to the toxin.

In the present application, the first polypeptide chain may form an immunoconjugate with the fusion polypeptide.

In the present application, the immunoconjugate may not include the first intein fragment and may not include the second intein fragment.

In the immunoconjugate of the present application, the first polypeptide chain and the fusion polypeptide may be combined with each other through the first antigen binding unit and the second antigen binding unit to form the immunoconjugate. For example, the first antigen binding unit may be connected to the second antigen binding unit through a disulfide bond between the variable region of the antibody light chain and the variable region of the antibody heavy chain. For example, the first antigen binding unit and the second antigen binding unit may be derived from trastuzumab. For example, the first antigen binding unit may be the light chain of trastuzumab, and the second antigen binding unit may be the variable region and constant region CH1 region of the heavy chain of trastuzumab. For example, the first antigen binding unit may include the amino acid sequence shown in SEQ ID NO: 3, and the second antigen binding unit may include the amino acid sequence shown in SEQ ID NO: 5. In the present application, the antigen-binding part may be the Fab of trastuzumab.

In the immunoconjugate of the present application, the C-terminus of the shielding peptide may be directly or indirectly connected to the N-terminus of the cleavable part.

In the immunoconjugate of the present application, the C-terminus of the cleavable part may be directly or indirectly connected to the N-terminus of the antigen-binding part.

In the immunoconjugate of the present application, the C-terminus of the antigen-binding part may be directly or indirectly connected to the N-terminus of the toxin. In the present application, the indirect connection may include connection through a linker. For example, the linker may comprise a peptide linker. For example, the peptide linker may include the amino acid sequence shown in SEQ ID NO:11.

In the immunoconjugate of the present application, it may include the shielding peptide, the cleavable part, the antigen-binding part, and the toxin in sequence from the N-terminus to the C-terminus. For example, it may sequentially include the shielding peptide, the cleavable part, the antigen-binding part, the linker and the toxin from the N-terminus to the C-terminus. For example, the toxin component may sequentially include the shielding peptide (which may include the amino acid sequence shown in SEQ ID NO: 1), the cleavable part (which may include the amino acid sequence shown in SEQ ID NO: 2), the antigen-binding part (trastuzumab Fab, which may include the amino acid sequence shown in SEQ ID NO: 3 and SEQ ID NO: 5), the linker (which may include SEQ ID NO: 11) and the toxin (PE24, which may include the amino acid sequence shown in SEQ ID NO: 9) from the N-terminus to the C-terminus.

For example, the immunoconjugate may be M-Fab-PE24, which may include the amino acid sequences shown in SEQ ID NO: 4 and SEQ ID NO: 12. In the present application, the immunoconjugate may comprise the amino acid sequence shown in SEQ ID NO: 4 and SEQ ID NO: 12.

Preparation Method

In the present application, the method may include the step of providing the targeting component, which may include: providing a first polypeptide chain comprising the shielding peptide and the first antigen binding unit, the shielding peptide and the first antigen binding unit are connected by the cleavable part; providing a second polypeptide chain comprising a second antigen binding unit and the first intein fragment, the second antigen binding unit is directly or indirectly connected to the first intein fragment; and the first polypeptide chain and the second polypeptide chain are combined to form the targeting component, wherein the first antigen binding unit of the first polypeptide chain and the second antigen binding unit of the second polypeptide chain bind to each other to form the antigen-binding part in the targeting component.

In the present application, step 3) of the method may also include the formation of a fusion polypeptide containing the second antigen-binding unit and the toxin by interaction between the first containing peptide fragment and the second containing peptide fragment, and the fusion polypeptide and the first polypeptide chain constitute the immunoconjugate.

In the present application, the method may use a reducing agent to initiate the interaction between the first intein fragment and the second intein fragment.

For example, the reducing agent may be selected from the following group: DTT and β-mercaptoethanol.

In the present application, the concentration of the reducing agent may be 0.1-100 nM (for example, it may be about 0.1-80 nM, about 0.1-60 nM, about 0.1-40 nM, about 0.1-20 nM, about 0.1-10 nM or about 1-10 nM).

In the present application, the reducing agent may be in contact with the targeting component and the toxin component. In the present application, the step of adding the reducing agent may occur at the same time as steps 1), 2) and 3) in the method or at different times. In the present application, after adding the reducing agent, the polypeptide combination may contain toxins with biological toxicity, and/or with biological toxicity.

In the present application, the method for preparing the immunoconjugate may further include incubating after adding the reducing agent. In the present application, the temperature of the incubation may be about 1 to about 50° C. (for example, it may be about 1° C. to about 50° C., about 4° C. to about 50° C., about 4° C. to about 45° C., about 4° C. to about 40° C., about 4° C. to about 37° C., about 8° C. to about 37° C., about 13° C. to about 37° C., about 17° C. to about 37° C., about 17° C. to about 35° C., about 17° C. to about 30° C., about 17° C. to about 25° C., about 17° C. to about 23° C., or about 20° C. to about 23° C.). In the present application, the incubation time is about 60 to about 300 minutes (for example, it may be about 60 to about 300 minutes, about 60 to about 240 minutes, about 60 to about 180 minutes, about 60 to about 120 minutes, about 90 to about 120 minutes).

Vector, Cells, and Pharmaceutical Uses

The application provides a vector comprising the nucleic acid encoding the first polypeptide chain in the polypeptide combination, the nucleic acid encoding the second polypeptide chain in the polypeptide combination, the nucleic acid encoding the toxin component in the polypeptide combination, the nucleic acid encoding the cleavable part of the polypeptide combination, the nucleic acid encoding the first antigen binding unit in the polypeptide combination, the nucleic acid encoding the second antigen-binding unit in the polypeptide combination, the nucleic acid encoding the first intein fragment in the polypeptide combination, the nucleic acid that encodes the second intein fragment in the polypeptide combination, and the nucleic acid of the toxin described in and/or the nucleic acid encoding the shielding peptide described in the polypeptide combination.

The present application provides a cell expressing the vector.

The application also provides a kit, which may include the first polypeptide chain, the second polypeptide chain, the toxin component, the cleavable part, the first antigen binding unit, the second antigen binding unit, the first intein fragment, the second intein fragment, the toxin, and one or more of the shielding peptide. In the present application, the components in the kit may not be mixed with each other. For example, the components in the kit may be placed in different containers and/or different physical spaces.

In the present application, the kit may also include a reducing agent. The reducing agent may be selected from the following group: DTT and β-mercaptoethanol. In the present application, the reducing agent may be contained in a separate container.

The application provides the use of the polypeptide combination, the vector or the cell in the preparation of a medicine for the treatment of diseases, the diseases include tumors.

For example, the treatment may include inhibiting or delaying the development or progression of tumors. For example, the treatment may reduce the size of the tumor (or even substantially eliminate the tumor), and/or may reduce and/or stabilize the disease state.

In the present application, the tumor may include ovarian cancer and breast cancer.

The application provides the polypeptide combination, the vector or the cell, which treats tumors.

The present application provides a method for treating tumors, which comprises administrating the polypeptide combination, the vector or the cell.

In the present application, the method may be implemented under in vivo conditions. For example, the first polypeptide chain, the second polypeptide chain, and the toxin component in the polypeptide combination may form the biologically toxic immunoconjugate under the conditions of the tumor cell microenvironment. In the present application, the immunoconjugate may have biological toxicity, for example, it may have a killing effect on tumor cells, or promote tumor cell apoptosis.

In the present application, the mode of administration may include oral administration, intravenous administration, intramuscular administration, in situ administration at the tumor site, inhalation, rectal administration, vaginal administration, transdermal administration and/or administration via sub cutaneous depot.

The present application also provides a method for administrating the polypeptide combination to cells, which may include the following steps: mixing and administrating the first polypeptide chain, the second polypeptide chain, the toxin component, and the reducing agent. Under in vitro conditions, the first polypeptide chain, the second polypeptide chain, and the toxin component form the immunoconjugate under reducing conditions. In the present application, the immunoconjugate may have biological toxicity, for example, it may have a killing effect on tumor cells, or promote tumor cell apoptosis.

The present application also provides a method for administrating the immunoconjugate to cells, which may include the following steps, administrating the immunoconjugate to cells under in vitro conditions.

Without intending to be limited by any theory, the following examples are only used to illustrate the fusion protein, preparation method, use, etc. of the present application, and are not used to limit the scope of the present application.

EXAMPLES

Example 1

Preparation and Activation of Antigen Shielding Immunotoxin 1.1 Construction of Expression Vector Using trastuzumab light chain and heavy chain, Npu DnaE intein, and synthetic PE24 gene sequence as templates, design PCR amplification primers, and add restriction endonuclease sites and protective bases at the 5'end of the inserted vector primers for the insertion of expression vectors.

The PCR synthesis fragment and the PM09 plasmid after restriction double digestion were ligated by DNA ligase to form PM-LC, PM-MLC, PM-HC-In eukaryotic vectors, respectively.

Among them, the PM-LC eukaryotic vector expresses the light chain of trastuzumab (LC, whose amino acid sequence is shown in SEQ ID NO. 3); the PM-MLC eukaryotic vector expresses the light chain of trastuzumab linked to the shielding peptide (MLC, whose amino acid sequence is shown in SEQ ID NO. 4); PM-HC-In eukaryotic vector expresses the heavy chain of trastuzumab (HC- In, whose amino acid sequence is shown in SEQ ID NO. 7).

The PCR synthesis fragment was ligated with the pET32a plasmid after restriction double digestion by DNA ligase to form the pET-Ic-PE24 prokaryotic expression vector.

Among them, the pET-Ic-PE24 prokaryotic expression vector expresses the PE24 toxin (Ic-PE24, whose amino acid sequence is shown in SEQ ID NO. 10) connected with the second intein fragment.

1.2 Expression and Purification of Target Protein

The vector PM-LC and PM-HC-In prepared in Example 1.1, or PM-MLC and PM-HC-In were co-transfected into mammalian cells HEK293E, so that the transfected cells expressed Trastuzumab Fab-Fab-In connected the first intein fragments and Trastuzumab Fab-MFab-In connected with shielding peptide and the first intein fragment.

Seven days after transfection, the cell culture supernatant was collected by centrifugation, filtered by a 0.45-micron filter membrane, and purified on a Capto L column.

The vector pET-Ic-PE24 prepared in Example 1.1 was transformed into *E. coli* competent BL21 (DE3), and the PE24 toxin connected with the second intein fragment—lc-PE24 was induced by IPTG. The expression cells were collected, and after high-pressure homogenization of the bacteria, the supernatant was collected by centrifugation and purified by a nickel column.

SDS-PAGE detects purified antibody fragments and toxin fragments. The results are shown in FIG. 1, where M represents marker, lane 1 is MFab-In, lane 2 is Ic-PE24, lane 3 is a mixture of M-Fab-ln and 1cPE24, and Lane 4 is a mix of MFAB-in and 1C-PE24 with 1mM DTT added.

1.3 Preparation of Antigen-Shielding Immunotoxin

The protein Fab-In or MFab-In prepared in Example 1.2 was reacted with the Ic-PE24 prepared in Example 1.2, and 1 mM DTT reducing agent was added to induce the protein trans-splicing reaction mediated by the first intein fragment and the second intein fragment, oxidized glutathione was added to terminate the reaction after the reaction at 37V for 2 h, and the disulfide bonds were oxidized to form, thus the immune conjugate-FAB-PE24 and M-Fab-PE24 were obtained, respectively.

Wherein, the immunoconjugate Fab-PE24 comprises trastuzumab Fab and the toxin PE24 linked thereto, and its amino acid sequence is shown in SEQ ID NO. 3 and SEQ ID NO. 12; the immunoconjugate M-Fab-PE24 comprises a shielding peptide, a cleavable part, trastuzumab Fab and a toxin PE24 linked thereto, and its amino acid sequence is as shown in SEQ ID NO. 4 and SEQ ID NO. 12.

Figure 2:
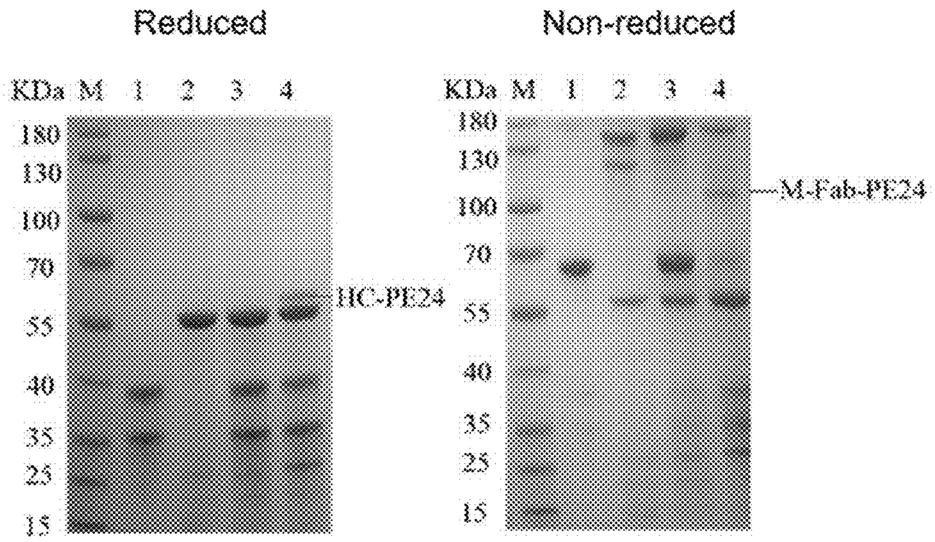
FIG. 2 shows the result of SDS-PAGE detection of the immunoconjugates in the present application.

SDS-PAGE detects the product of protein trans-splicing reaction. The results are shown in FIG. 2, where M stands for marker, lane 1 is M-Fab-PE24, lane 2 is M-Fab-PE24 treated with uPA (Urokinase type plasminogen activator).

1.4 Activation of Antigen-Shielding Immunotoxin uPA freeze-dried powder (as a protease, which can cleavage the cleavable part of the shielding peptide) is dissolved in sterile PBS to prepare a 140 μg/ml protease solution.

The M-Fab-PE24 prepared in Example 1.3 was treated with uPA, 150 μg M-Fab-PE24 was mixed with 8 μL protease solution, and reacted overnight at 37° C. in a water bath.

Figure 3:
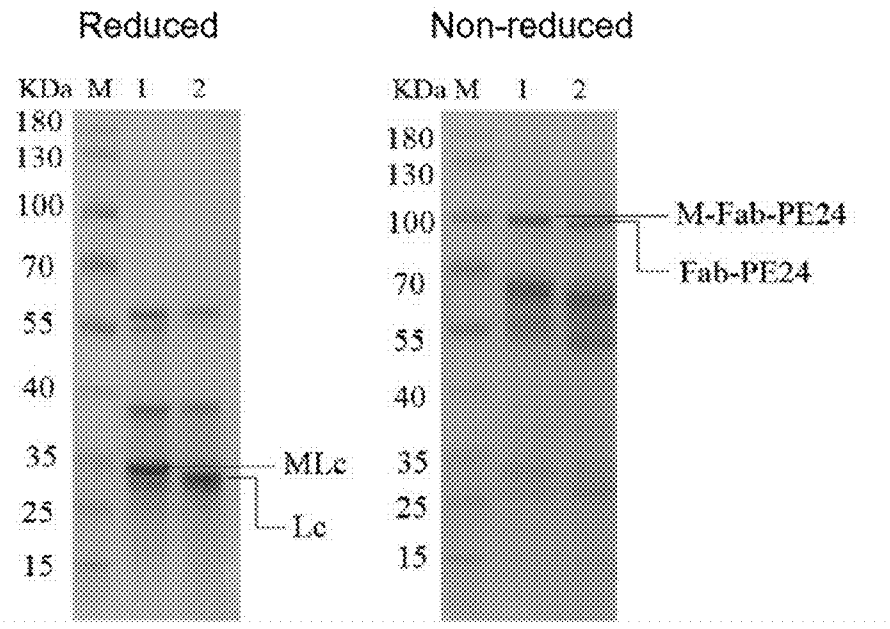
FIG. 3 shows the result of SDS-PAGE detection of the immunoconjugate in the present application activated after protease treatment.

SDS-PAGE detects the reaction products. The results are shown in FIG. 3, where lane 1 is M-Fab-PE24 and lane 2 is M-Fab-PE24 treated with uPA (also known as activated M-Fab-PE24).

Example 2

Antigen Affinity Analysis

The logarithmic growth cells BT-474 (human breast cancer cells purchased from ATCC®HTB-20™), SKOV-3 (human ovarian cells purchased from ATCC®HTB-77™) and McF-7 (human breast cancer cells purchased from ATCC®HTB-22TM) were digested with trypsin and counted.

Take $1\times10^6$ cells from each sample for subsequent experiments; centrifuge at 1,500 rpm at 4° C. for 5 min, discard the supernatant, and resuspend the cells in 100 μL of flow cytometry solution; add 1 μL trastuzumab (expression and purification by members of our research group) or Fab-PE24 or M-Fab-PE24 prepared in Example 1 respectively.

Incubate the cell samples for 30 min at 4° C.; centrifuge at 1,500 rpm for 5 minutes at 4° C., discard the supernatant, resuspend in 1 mL PBS +2% FBS and wash three times; centrifuge at 4° C., 1,500 rpm for 5 min, discard the supernatant, and resuspend the cells to 100 μL flow cytometry working solution; add 1 μL FITC fluorescently labeled fluorescent antibody that recognizes human IgG.

Cell samples were incubated for 30 min at 4° C.; centrifuged at 1,500 rpm at 4° C. for 5 min, discarded the supernatant, resuspended in 1 mL PBS +2% FBS and washed three times; centrifuged at 4° C. at 1,500 rpm for 5 min, removed the supernatant, and resuspended in 0.5 mL PBS +2% FBS and flow cytometry within 4 hours with FITC channel detection.

Figure 4:
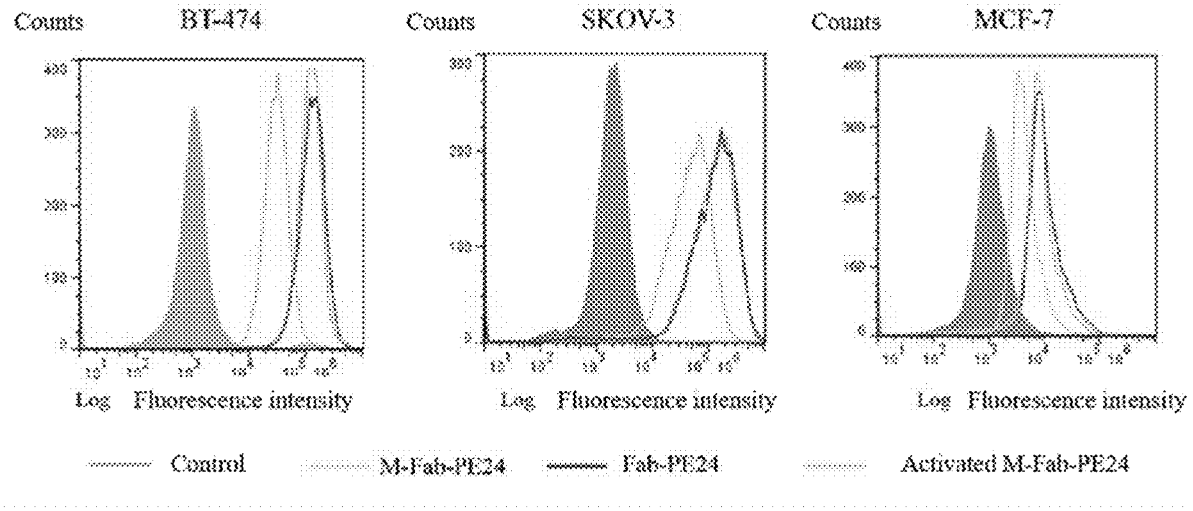
FIG. 4 shows the result of the binding affinity analysis of the immunoconjugate in the present application to tumor cells expressing the HER2/erbB2/neu antigen.

The results are shown in FIG. 4. As the logarithmic fluorescence intensity increases, M-Fab-PE24 will first break away from the specific binding to tumor cells BT-474, SKOV-3 and MCF-7, and further enhance the logarithmic fluorescence intensity. Fab-PE24 and activated M-Fab-PE24 then broke away from the specific binding to tumor cells BT-474, SKOV-3 and MCF-7. The results showed that compared with Fab-PE24, the antigen affinity of M-Fab-PE24 decreased significantly, and the antigen affinity of activated M-Fab-PE24 recovered to a level equivalent to that of Fab-PE24 after protease treatment.

Example 3

Cytotoxicity Analysis

Digest the tumor cells BT-474, SKOV-3 and MCF-7 in logarithmic growth phase with 0.25% trypsin, pipette to mix them, transfer them to a 50 mL centrifuge tube with a pipette, and determine the cell viability and density. Among them, the viability of tumor cells used for cell killing needs to reach more than 95%.

Record the cell suspension volume and collect the cells in a 50 mL centrifuge tube, centrifuge at 1,000 rpm for 5 minutes at room temperature in a benchtop centrifuge; dilute the cell suspension according to the plating density required for different tumor cells, mix the cells thoroughly, and add to 96-well cell culture plate (5.0×103 cells/well), gently shake the cell culture plate to distribute the cells evenly, and then place it in a 37° C., 5% $CO_2$ cell incubator overnight (16-20 hours).

Each group of cells was added with the immunoconjugate Fab-PE24 or M-Fab-PE24 prepared in Example 1, and incubated at 37° C. for 72 hours.

Remove the original culture medium, add 100 μL of fresh culture medium, 10 μL of CCK8 solution; incubate in a 37° C. incubator for 1 hour. The absorbance value of each group of cells at 450 nm wavelength was detected by a microplate reader to calculate the cell viability of each group. The results are shown in FIG. 5.

Figure 5:
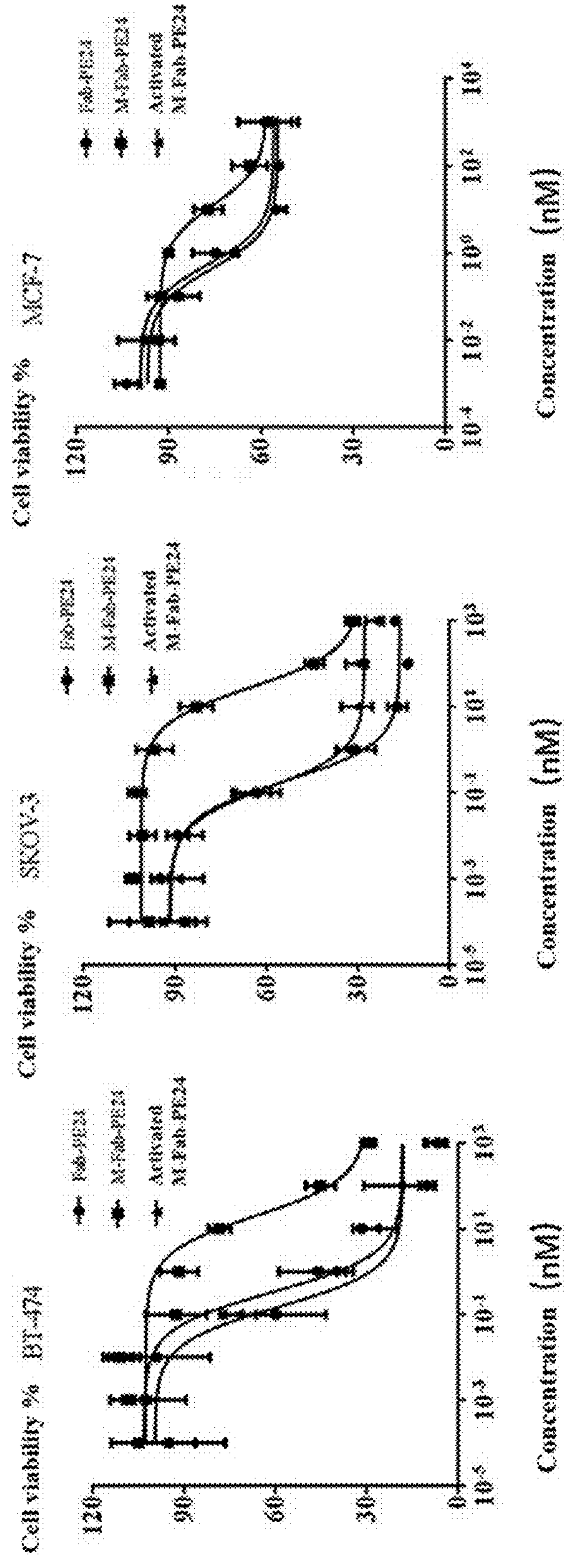
FIG. 5 shows the result of the cytotoxicity analysis of the immunoconjugate in the present application on tumor cells expressing HER2/erbB2/neu antigen.

As shown in FIG. 5, as the concentration of Fab-PE24 or M-Fab-PE24 increased, the cell viability of tumor cells BT-474, SKOV-3 and MCF-7 all decreased. Among them, compared with Fab-PE24, the cytotoxicity caused by M-Fab-PE24 was significantly reduced, and the cytotoxicity caused by M-Fab-PE24 activated after protease treatment showed recovery. See Table 1 for the IC50 of each group of immunotoxins.

TABLE 1

| | $IC_{50}$ (nM) | | |
|---|---|---|---|
| Cell line | Fab-PE24 | M-Fab-PE24 | Activated M-Fab-PE24 |
| BT-474 | 0.15 ± 0.04 | 19.90 ± 2.45 | 0.33 ± 0.27 |
| SKOV-3 | 0.19 ± 0.05 | 28.00 ± 3.05 | 0.13 ± 0.07 |
| MCF-7 | 0.53 ± 0.12 | 12.81 ± 1.7 | 0.44 ± 0.36 |

Example 4

In vivo Pharmacodynamic Evaluation

Balb/c nude mice (purchased from Shanghai Slack Laboratory Animal Co., Ltd.) were inoculated with SK-OV3 tumor cells about 10 days after the tumor volume reached an average of 100 mm3. They were randomly divided into four groups and injected with PBS, FAB-PE24 (1.0 mg/kg), M-FAB-PE24 (1.0 mg/kg) and NCM-FAB-PE24 (1.0 mg/kg) prepared in example 1 respectively.

Among them, the difference between NCM-Fab-PE24 and M-Fab-PE24 is that the former is connected to the cleavable part of the shielding peptide without restriction sites, so the shielding peptide will not be removed. The amino acid sequence of NCM-Fab-PE24 is shown in SEQ ID NO.13 and SEQ ID NO.12.

It is administrated by intravenous injection, once every other day, for a total of six times. The body weight and tumor volume of the mice were measured before each administration. After the administration, the body weight and tumor volume of the mice were measured twice a week. When the maximum tumor volume reached 1000 $mm^3$, the experiment was terminated and the mice were euthanized, and the nodules were peeled off.

Figure 6:
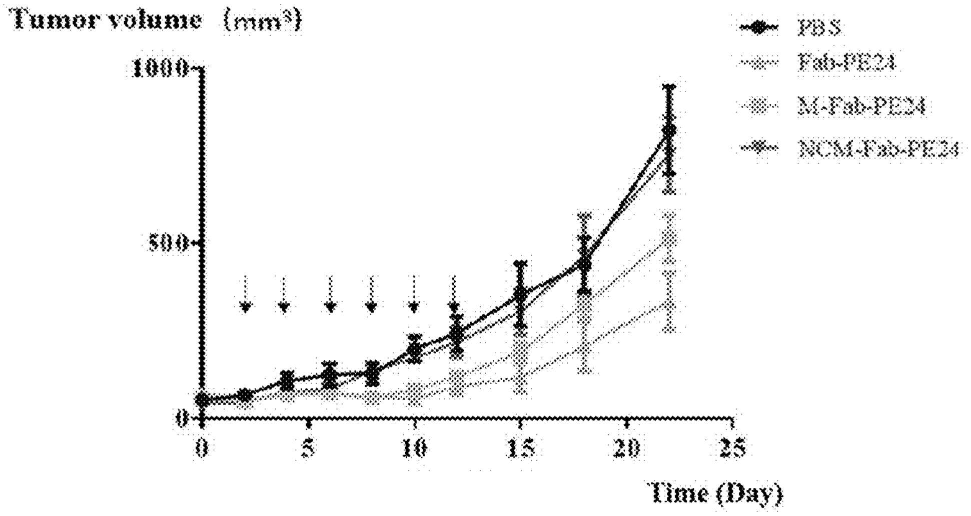
FIG. 6 shows the result of the in vivo pharmacodynamic study of the immunoconjugates in the present application.

The tumor volume changes of mice in each group are shown in FIG. 6. As shown in FIG. 6, during the administration period, the tumor in the PBS control group grew faster, and NCM-Fab-PE24 had no obvious therapeutic effect. The inhibitory effects of Fab-PE24 and M-Fab-PE24 on tumors were more obvious. Among them, the anti-tumor effect of M-Fab-PE24 is equivalent to that of Fab-PE24.

Example 5

Tumor Distribution

During the treatment of tumor-bearing Balb/c nude mice receiving the Fab-PE24 and M-Fab-PE24 prepared in Example 1, after the third administration (wherein, the dosage, method of administration and drug frequency during the treatment could see Example 4), the mice were euthanized the next day, and the tumor tissue was taken out and embedded in OCT and then frozen, Use a cryostat to perform frozen sections and perform immunofluorescence staining analysis on the sections. The specific steps are as follows:

Tissue sections were fixed with pre-chilled 4% (v/v) paraformaldehyde and fixed at 4° C. for 10 minutes; the sections were washed with PBS for 10 minutes, and the PBS was blotted dry with absorbent paper. Incubate the sections with blocking solution (PBS containing 1% (v/v) horse serum) for 30 min at room temperature; diluent for the primary antibody (rabbit anti-ETA antibody) (PBS containing 1% bovine serum albumin, 0.3% TritonX-100) After dilution, incubate the slices overnight at 4° C.; wash the slices 3 times with PBS for 15 min each; after diluting the secondary antibody (PE conjugated goat anti rabbit antibody) with the diluent, drop it onto the surface of the slices, and incubate the slices for 1 hour at room temperature; PBS washed the sections 3 times, 15 min each time; the sections were counterstained with DAPI for 5 min at room temperature; the sections were washed with PBS for 10 min; the sections were observed with a fluorescence microscope.

Figure 7:
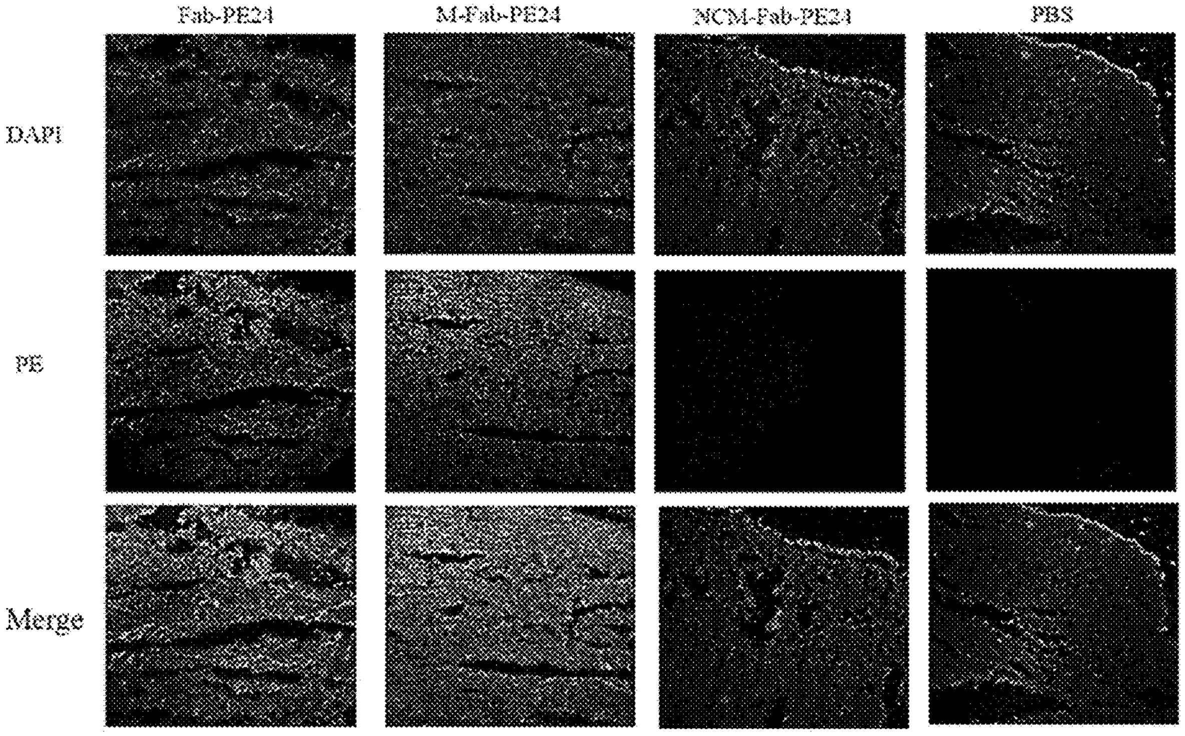
FIG. 7 shows the tumor volume in SKOV-3 tumor-bearing mice after administration of the immunoconjugate in the present application.

See FIG. 7 for the distribution of tumors after treatment in each group. The results in FIG. 7 show that fluorescence can be observed in both the Fab-PE24 group and the M-Fab-PE24 group, indicating that both the immunoconjugates Fab-PE24 and M-Fab-PE24 can penetrate into tumor tissues, while NCM-Fab-PE24 has almost no distribution in tumor tissues. This means that the immunoconjugate M-Fab-PE24 with the shielding peptide can restore the antigen-specific binding under the action of the tumor microenvironment protease. However, only the nucleus-stained DAPI fluorescence can be observed on the tumor slices of the PBS group treated with the same antibody. This result shows that the results of FIG. 7 can exclude the interference of the antibody itself on the non-specific binding of the tissue.

Example 6

Hepatotoxicity Analysis

A kit (purchased from Nanjing Jiancheng Biological Co., Ltd.) was used to detect the activities of alanine aminotransferase (AST) and aspartate aminotransferase (ALT) in mouse serum. The AST and ALT levels of each group of mice reflect the toxic effect of the immunoconjugate prepared in Example 1 on the liver of mice. Therefore, AST and ALT can be used as indicators for evaluating the non-specific toxicity of the immunoconjugate.

Figure 8:
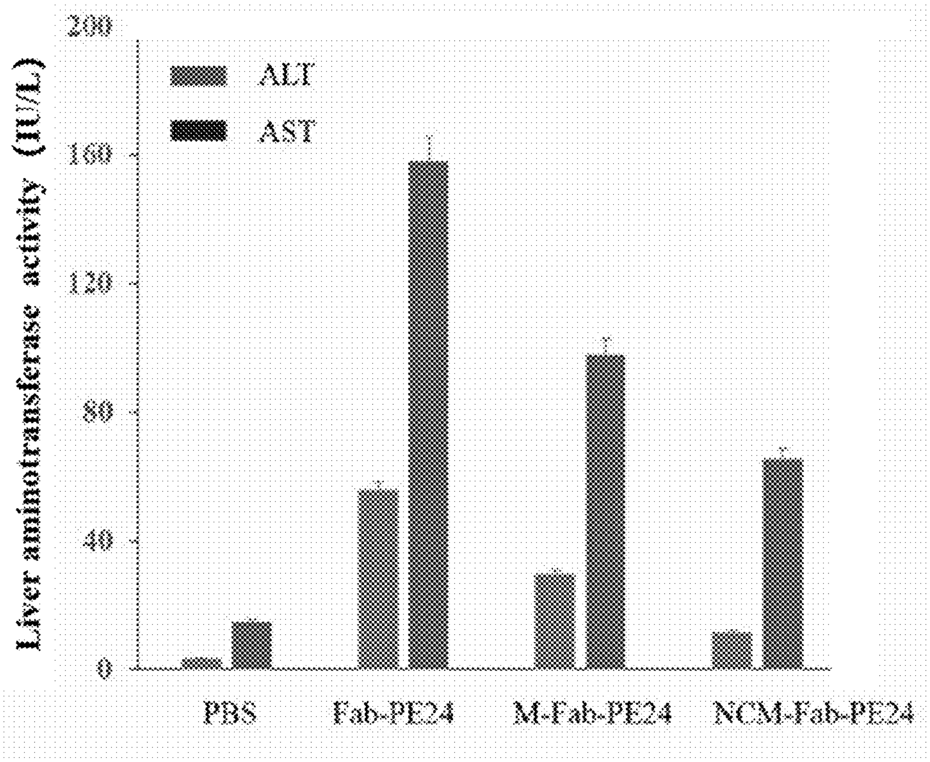
FIG. 8 shows the result of the damage test of the immunoconjugate in the present application on the liver tissue of mice.

The experimental results are shown in FIG. 8. Compared with the PBS control group, the immunoconjugates Fab-PE24 and M-Fab-PE24 both lead to increased serum transaminase activity, and there are significant differences between the three groups; however, the AST and ALT levels of the Fab-PE24 group were significantly higher than those of the M-Fab-PE24 group. This shows that Fab-PE24 has a greater effect on liver tissue damage than M-Fab-PE24.

The foregoing detailed description is provided by way of explanation and examples, and is not intended to limit the scope of the appended claims. Various changes of the implementation manners listed in the present application are obvious to those of ordinary skill in the art, and are reserved within the scope of the appended claims and their equivalents.

The invention claimed is:

1. A polypeptide combination, which includes a targeting component and a toxin component, wherein:

said targeting component includes a shielding peptide, a cleavable part, an antigen-binding part, and a first intein fragment, said shielding peptide and said antigen-binding part are connected by said cleavable part, and said antigen-binding part is directly or indirectly connected with said first intein fragment;

said toxin component comprises a second intein fragment and a toxin, and said second intein fragment is directly or indirectly connected to said toxin;

said targeting component and said toxin component are able to form an immunoconjugate through an interaction between said first intein fragment and said second intein fragment;

said immunoconjugate comprises said shielding peptide, said antigen-binding part and said toxin, wherein said shielding peptide is connected with said antigen-binding part through said cleavable part, and said antigen-binding part is directly or indirectly connected with said toxin.

2. The polypeptide combination of claim 1, wherein said targeting component comprises a first polypeptide chain and a second polypeptide chain; said first polypeptide chain comprises said shielding peptide and the first antigen binding unit, and said shielding peptide is connected with said first antigen binding unit through said cleavable part; said second polypeptide chain comprises a second antigen binding unit and said first intein fragment, and said second antigen binding unit is directly or indirectly connected with said first intein fragment; and said first antigen binding unit and said second antigen binding unit are able to combine with each other to form said antigen-binding part.

3. The polypeptide combination of claim 2, wherein said second polypeptide chain and said toxin component are able to form a fusion polypeptide containing said second antigen binding unit and said toxin through an interaction between said first intein fragment and said second intein fragment; in said fusion polypeptide, said second antigen binding unit is directly or indirectly connected with said toxin; and said first polypeptide chain and said fusion polypeptide constitute said immunoconjugate.

4. The polypeptide combination of claim 1,
wherein said immunoconjugate does not comprise said first intein fragment and does not comprise said second intein fragment.

5. The polypeptide combination of claim 1,
wherein in said immunoconjugate, the C-terminus of said shielding peptide is directly or indirectly connected to the N-terminus of said cleavable part.

6. The polypeptide combination of claim 1,
wherein in said immunoconjugate, the C-terminus of said cleavable part is directly or indirectly connected to the N-terminus of said antigen-binding part.

7. The polypeptide combination of claim 1,
wherein in said immunoconjugate, the C-terminus of said antigen-binding part is directly or indirectly connected to the N-terminus of said toxin.

8. The polypeptide combination of claim 3,
wherein in said immunoconjugate, said first polypeptide chain and said fusion polypeptide form said immunoconjugate through a mutual combination of said first antigen binding unit and said second antigen binding unit.

9. The peptide combination of claim 1, wherein
said shielding peptide is selected from the following group: a HER2 antigen shielding peptide, an EGFR antigen shielding peptide, an EpCAM antigen shielding peptide, and a mesothelin antigen shielding peptide.

10. The polypeptide combination of claim 1,
wherein said cleavable part is selected from the following group: a matrix metalloproteinase sensitive linker, a serine protease sensitive linker and an urokinase plasminogen activator sensitive linker.

11. The polypeptide combination of claim 1,
wherein said targeting component targets a tumor specific antigen.

12. The polypeptide combination of claim 1,
wherein said antigen-binding part comprises an antibody or an antigen binding fragment.

13. The polypeptide combination of claim 1,
wherein said toxin is selected from the following group: a bacterial toxin, a human toxin and a plant toxin.

14. The polypeptide combination of claim 1,
wherein said first intein fragment and/or said second intein fragment comprise a fragmented intein.

15. A method for preparing an immunoconjugate, comprising the following steps:

1) Providing a targeting component, said targeting component comprises a shielding peptide, a said cleavable part, an antigen-binding part and a first intein fragment, said shielding peptide is connected with said antigen-binding part through said cleavable part, and said antigen-binding part is directly or indirectly connected with said first intein fragment;
2) Providing a toxin component comprising a second intein fragment and a toxin, and said second intein fragment is directly or indirectly connected with said toxin;
3) Contacting said targeted component and said toxin component under the condition that said first intein fragment and said second intein fragment are able to interact, wherein said targeted component and said toxin component form said immunoconjugate through an interaction between said first intein fragment and said second intein fragment.

16. The method of claim 15, wherein said providing a targeting component comprises:

providing a first polypeptide chain, said first polypeptide chain comprises said shielding peptide and a first antigen binding unit, said shielding peptide and said first antigen binding unit are connected by said cleavable part;

providing a second polypeptide chain, said second polypeptide chain comprises a second antigen binding unit and said first intein fragment, and said second antigen binding unit is directly or indirectly connected to said first intein fragment; and combining said first polypeptide chain and said second polypeptide chain to form said targeted component, wherein said first antigen binding unit of said first polypeptide chain and said second antigen binding unit of said second polypeptide chain are combined with each other to form said antigen-binding part of said targeted component.

17. The method of claim 16, wherein 3) comprises making said second polypeptide chain and said toxin component form a fusion polypeptide containing said second antigen binding unit and said toxin through an interaction between said first intein fragment and said second intein fragment, and said fusion polypeptide and said first polypeptide chain form said immunoconjugate.

18. The method of claim 15, wherein said interaction between said first intein fragment and said second intein fragment comprises trans splicing reaction.

19. The method of claim 15, wherein a reducing agent is used to trigger said interaction between said first intein fragment and said second intein fragment.

20. A method for treating a tumor, which comprises administrating the polypeptide combination of claim 1.

* * * * *

SEQUENCE LISTING

<160> NUMBER OF SEQ ID NOS: 13

<210> SEQ ID NO 1
<211> LENGTH: 10
<212> TYPE: PRT
<213> ORGANISM: Artificial Sequence
<220> FEATURE:
<223> OTHER INFORMATION: Shielding peptide M

<400> SEQUENCE: 1

```
Gln Met Trp Ala Pro Gln Trp Gly Pro Asp
1               5                   10
```

<210> SEQ ID NO 2
<211> LENGTH: 26
<212> TYPE: PRT
<213> ORGANISM: Artificial Sequence
<220> FEATURE:
<223> OTHER INFORMATION: the cleavable portion

<400> SEQUENCE: 2

```
Gly Ser Ser Gly Gly Ser Gly Gly Ser Gly Gly Ser Gly Leu Ser Gly
1               5                   10                  15

Arg Ser Asp Asn His Gly Ser Ser Gly Thr
            20                  25
```

<210> SEQ ID NO 3
<211> LENGTH: 214
<212> TYPE: PRT
<213> ORGANISM: Artificial Sequence
<220> FEATURE:
<223> OTHER INFORMATION: the first antigen binding unit LC(Trastuzumab)

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 4
<211> LENGTH: 250
<212> TYPE: PRT
<213> ORGANISM: Artificial Sequence
<220> FEATURE:
<223> OTHER INFORMATION: the first polypeptide chain MLC (Trastuzumab)
      (comprising M, the cleavable portion, LC)

<400> SEQUENCE: 4

Gln Met Trp Ala Pro Gln Trp Gly Pro Asp Gly Ser Ser Gly Gly Ser
1               5                   10                  15

Gly Gly Ser Gly Gly Ser Gly Leu Ser Gly Arg Ser Asp Asn His Gly
            20                  25                  30

Ser Ser Gly Thr Asp Ile Gln Met Thr Gln Ser Pro Ser Ser Leu Ser
        35                  40                  45

Ala Ser Val Gly Asp Arg Val Thr Ile Thr Cys Arg Ala Ser Gln Asp
    50                  55                  60

Val Asn Thr Ala Val Ala Trp Tyr Gln Gln Lys Pro Gly Lys Ala Pro
65                  70                  75                  80

Lys Leu Leu Ile Tyr Ser Ala Ser Phe Leu Tyr Ser Gly Val Pro Ser
                85                  90                  95

Arg Phe Ser Gly Ser Arg Ser Gly Thr Asp Phe Thr Leu Thr Ile Ser
            100                 105                 110

Ser Leu Gln Pro Glu Asp Phe Ala Thr Tyr Tyr Cys Gln Gln His Tyr
        115                 120                 125

Thr Thr Pro Pro Thr Phe Gly Gln Gly Thr Lys Val Glu Ile Lys Arg
    130                 135                 140

Thr Val Ala Ala Pro Ser Val Phe Ile Phe Pro Pro Ser Asp Glu Gln
145                 150                 155                 160

Leu Lys Ser Gly Thr Ala Ser Val Val Cys Leu Leu Asn Asn Phe Tyr
                165                 170                 175

Pro Arg Glu Ala Lys Val Gln Trp Lys Val Asp Asn Ala Leu Gln Ser
            180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
                245                 250


<210> SEQ ID NO 5
<211> LENGTH: 226
<212> TYPE: PRT
<213> ORGANISM: Artificial Sequence
<220> FEATURE:
<223> OTHER INFORMATION: the second antigen binding unit HC
      (Trastuzumab)

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr
225
```

<210> SEQ ID NO 6
<211> LENGTH: 102
<212> TYPE: PRT
<213> ORGANISM: Artificial Sequence
<220> FEATURE:
<223> OTHER INFORMATION: the first intein fragment In

<400> SEQUENCE: 6

```
Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100
```

<210> SEQ ID NO 7
<211> LENGTH: 328
<212> TYPE: PRT
<213> ORGANISM: Artificial Sequence
<220> FEATURE:
<223> OTHER INFORMATION: the second polypeptide chain (HC-In
      Trastuzumab)

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr Cys Leu Ser Tyr Glu Thr Glu Ile Leu Thr Val Glu Tyr Gly
225                 230                 235                 240

Leu Leu Pro Ile Gly Lys Ile Val Glu Lys Arg Ile Glu Cys Thr Val
                245                 250                 255

Tyr Ser Val Asp Asn Asn Gly Asn Ile Tyr Thr Gln Pro Val Ala Gln
            260                 265                 270

Trp His Asp Arg Gly Glu Gln Glu Val Phe Glu Tyr Cys Leu Glu Asp
        275                 280                 285

Gly Ser Leu Ile Arg Ala Thr Lys Asp His Lys Phe Met Thr Val Asp
    290                 295                 300

Gly Gln Met Leu Pro Ile Asp Glu Ile Phe Glu Arg Glu Leu Asp Leu
305                 310                 315                 320

Met Arg Val Asp Asn Leu Pro Asn
                325
```

<210> SEQ ID NO 8
<211> LENGTH: 39
<212> TYPE: PRT
<213> ORGANISM: Artificial Sequence
<220> FEATURE:
<223> OTHER INFORMATION: the second intein fragment Ic

<400> SEQUENCE: 8

```
Met Ile Lys Ile Ala Thr Arg Lys Tyr Leu Gly Lys Gln Asn Val Tyr
1               5                   10                  15
```

-continued

```
Asp Ile Gly Val Glu Arg Asp His Asn Phe Ala Leu Lys Asn Gly Phe
            20                  25                  30

Ile Ala Ser Asn Cys Phe Asn
        35


<210> SEQ ID NO 9
<211> LENGTH: 229
<212> TYPE: PRT
<213> ORGANISM: Artificial Sequence
<220> FEATURE:
<223> OTHER INFORMATION: toxin PE24

<400> SEQUENCE: 9

Arg His Arg Gln Pro Arg Gly Trp Glu Gln Leu Pro Thr Gly Ala Glu
1               5                   10                  15

Phe Leu Gly Asp Gly Gly Asp Val Ser Phe Ser Thr Arg Gly Thr Gln
            20                  25                  30

Asn Trp Thr Val Glu Arg Leu Leu Gln Ala His Ala Gln Leu Glu Glu
        35                  40                  45

Arg Gly Tyr Val Phe Val Gly Tyr His Gly Thr Ala Leu Glu Ala Ala
    50                  55                  60

Gln Ser Ile Val Phe Gly Gly Val Arg Ala Arg Ser Gln Asp Leu Ala
65                  70                  75                  80

Ala Ile Trp Ala Gly Phe Tyr Ile Ala Gly Asp Pro Ala His Ala Tyr
                85                  90                  95

Gly Tyr Ala Gln Asp Gln Glu Pro Asp Ala Ala Gly Arg Ile Ala Asn
            100                 105                 110

Gly Ala Leu Leu Arg Val Tyr Val Pro Ala Ser Ser Leu Pro Gly Phe
        115                 120                 125

Tyr Arg Thr Gly Leu Thr Leu Ala Ala Pro Glu Ala Ala Gly Glu Val
    130                 135                 140

Glu Arg Leu Ile Gly His Pro Leu Pro Leu Ala Leu Asp Ala Ile Thr
145                 150                 155                 160

Gly Pro Glu Glu Glu Gly Gly Arg Glu Glu Thr Ile Leu Gly Trp Pro
                165                 170                 175

Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Lys Glu
        195                 200                 205

Gln Ala Ile Ser Ala Leu Pro Asp Tyr Ala Ser Gln Pro Gly Lys Pro
    210                 215                 220

Pro Lys Asp Glu Leu
225


<210> SEQ ID NO 10
<211> LENGTH: 283
<212> TYPE: PRT
<213> ORGANISM: Artificial Sequence
<220> FEATURE:
<223> OTHER INFORMATION: toxin component (the second intein
      fragment+toxin PE24) (Ic-PE24)

<400> SEQUENCE: 10

Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30
```

-continued

```
Ile Ala Ser Asn Cys Phe Asn Gly Gly Gly Gly Ser Gly Gly Gly Gly
        35                  40                  45

Ser Gly Gly Gly Gly Ser Arg His Arg Gln Pro Arg Gly Trp Glu Gln
    50                  55                  60

Leu Pro Thr Gly Ala Glu Phe Leu Gly Asp Gly Gly Asp Val Ser Phe
65                  70                  75                  80

Ser Thr Arg Gly Thr Gln Asn Trp Thr Val Glu Arg Leu Leu Gln Ala
                85                  90                  95

His Ala Gln Leu Glu Glu Arg Gly Tyr Val Phe Val Gly Tyr His Gly
            100                 105                 110

Thr Ala Leu Glu Ala Ala Gln Ser Ile Val Phe Gly Gly Val Arg Ala
        115                 120                 125

Arg Ser Gln Asp Leu Ala Ala Ile Trp Ala Gly Phe Tyr Ile Ala Gly
    130                 135                 140

Asp Pro Ala His Ala Tyr Gly Tyr Ala Gln Asp Gln Glu Pro Asp Ala
145                 150                 155                 160

Ala Gly Arg Ile Ala Asn Gly Ala Leu Leu Arg Val Tyr Val Pro Ala
                165                 170                 175

Ser Ser Leu Pro Gly Phe Tyr Arg Thr Gly Leu Thr Leu Ala Ala Pro
            180                 185                 190

Glu Ala Ala Gly Glu Val Glu Arg Leu Ile Gly His Pro Leu Pro Leu
        195                 200                 205

Ala Leu Asp Ala Ile Thr Gly Pro Glu Glu Glu Gly Gly Arg Glu Glu
    210                 215                 220

Thr Ile Leu Gly Trp Pro Leu Ala Glu Arg Thr Val Val Ile Pro Ser
225                 230                 235                 240

Ala Ile Pro Thr Asp Pro Arg Asn Val Gly Gly Asp Leu Asp Pro Ser
                245                 250                 255

Ser Ile Pro Asp Lys Glu Gln Ala Ile Ser Ala Leu Pro Asp Tyr Ala
            260                 265                 270

Ser Gln Pro Gly Lys Pro Pro Lys Asp Glu Leu
        275                 280


<210> SEQ ID NO 11
<211> LENGTH: 15
<212> TYPE: PRT
<213> ORGANISM: Artificial Sequence
<220> FEATURE:
<223> OTHER INFORMATION: Connexon (link the second antigen binding
      fragment and toxin PE24)

<400> SEQUENCE: 11

Gly Gly Gly Gly Ser Gly Gly Gly Gly Ser Gly Gly Gly Gly Ser
1               5                   10                  15


<210> SEQ ID NO 12
<211> LENGTH: 470
<212> TYPE: PRT
<213> ORGANISM: Artificial Sequence
<220> FEATURE:
<223> OTHER INFORMATION: Fusion polypeptide (the second antigen binding
      fragment+toxin PE24 Trastuzumab) HC-PE24

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr Gly Gly Gly Gly Ser Gly Gly Gly Gly Ser Gly Gly Gly Gly
225                 230                 235                 240

Ser Arg His Arg Gln Pro Arg Gly Trp Glu Gln Leu Pro Thr Gly Ala
                245                 250                 255

Glu Phe Leu Gly Asp Gly Gly Asp Val Ser Phe Ser Thr Arg Gly Thr
            260                 265                 270

Gln Asn Trp Thr Val Glu Arg Leu Leu Gln Ala His Ala Gln Leu Glu
        275                 280                 285

Glu Arg Gly Tyr Val Phe Val Gly Tyr His Gly Thr Ala Leu Glu Ala
    290                 295                 300

Ala Gln Ser Ile Val Phe Gly Gly Val Arg Ala Arg Ser Gln Asp Leu
305                 310                 315                 320

Ala Ala Ile Trp Ala Gly Phe Tyr Ile Ala Gly Asp Pro Ala His Ala
                325                 330                 335

Tyr Gly Tyr Ala Gln Asp Gln Glu Pro Asp Ala Ala Gly Arg Ile Ala
            340                 345                 350

Asn Gly Ala Leu Leu Arg Val Tyr Val Pro Ala Ser Ser Leu Pro Gly
        355                 360                 365

Phe Tyr Arg Thr Gly Leu Thr Leu Ala Ala Pro Glu Ala Ala Gly Glu
    370                 375                 380

Val Glu Arg Leu Ile Gly His Pro Leu Pro Leu Ala Leu Asp Ala Ile
385                 390                 395                 400

Thr Gly Pro Glu Glu Glu Gly Gly Arg Glu Glu Thr Ile Leu Gly Trp
                405                 410                 415

Pro Leu Ala Glu Arg Thr Val Val Ile Pro Ser Ala Ile Pro Thr Asp
            420                 425                 430

Pro Arg Asn Val Gly Gly Asp Leu Asp Pro Ser Ser Ile Pro Asp Lys
        435                 440                 445
```

-continued

```
Glu Gln Ala Ile Ser Ala Leu Pro Asp Tyr Ala Ser Gln Pro Gly Lys
    450                 455                 460

Pro Pro Lys Asp Glu Leu
465                 470


<210> SEQ ID NO 13
<211> LENGTH: 240
<212> TYPE: PRT
<213> ORGANISM: Artificial Sequence
<220> FEATURE:
<223> OTHER INFORMATION: NCM-LC

<400> SEQUENCE: 13

Gln Met Trp Ala Pro Gln Trp Gly Pro Asp Gly Gly Gly Gly Ser Gly
1               5                   10                  15

Gly Gly Gly Ser Gly Gly Gly Gly Ser Gly Asp Ile Gln Met Thr Gln
            20                  25                  30

Ser Pro Ser Ser Leu Ser Ala Ser Val Gly Asp Arg Val Thr Ile Thr
        35                  40                  45

Cys Arg Ala Ser Gln Asp Val Asn Thr Ala Val Ala Trp Tyr Gln Gln
    50                  55                  60

Lys Pro Gly Lys Ala Pro Lys Leu Leu Ile Tyr Ser Ala Ser Phe Leu
65                  70                  75                  80

Tyr Ser Gly Val Pro Ser Arg Phe Ser Gly Ser Arg Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln His Tyr Thr Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```